(12) United States Patent
Liu et al.

(10) Patent No.: US 10,898,522 B2
(45) Date of Patent: Jan. 26, 2021

(54) COMPOSITIONS AND METHODS FOR TREATING GRAFT VERSUS HOST DISEASE

(71) Applicant: Children's Research Institute, Children's National Medical Center, Washington, DC (US)

(72) Inventors: Yang Liu, Washington, DC (US); Yin Wang, Washington, DC (US)

(73) Assignee: Children's Research Institute, Children's National Medical Center, Washington, DC (US)

(*) Notice: Subject to any disclaimer, the term of this patent is extended or adjusted under 35 U.S.C. 154(b) by 122 days.

(21) Appl. No.: 15/753,901

(22) PCT Filed: Aug. 18, 2016

(86) PCT No.: PCT/US2016/047595
§ 371 (c)(1),
(2) Date: Feb. 20, 2018

(87) PCT Pub. No.: WO2017/031341
PCT Pub. Date: Feb. 23, 2017

(65) Prior Publication Data
US 2018/0236002 A1  Aug. 23, 2018

Related U.S. Application Data

(60) Provisional application No. 62/207,000, filed on Aug. 19, 2015.

(51) Int. Cl.
| | |
|---|---|
| *A61K 35/28* | (2015.01) |
| *A61K 38/08* | (2019.01) |
| *A61K 38/17* | (2006.01) |
| *A61K 38/16* | (2006.01) |
| *A61P 37/06* | (2006.01) |
| *A61P 35/02* | (2006.01) |
| *A61K 31/7105* | (2006.01) |
| *A61K 48/00* | (2006.01) |

(52) U.S. Cl.
CPC .......... *A61K 35/28* (2013.01); *A61K 31/7105* (2013.01); *A61K 38/08* (2013.01); *A61K 38/164* (2013.01); *A61K 38/1709* (2013.01); *A61K 48/005* (2013.01); *A61P 35/02* (2018.01); *A61P 37/06* (2018.01); *A61K 2300/00* (2013.01)

(58) Field of Classification Search
None
See application file for complete search history.

(56) References Cited

U.S. PATENT DOCUMENTS

| | | | |
|---|---|---|---|
| 7,521,431 B2 * | 4/2009 | Reich | C12N 15/113 435/320.1 |
| 8,697,359 B1 | 4/2014 | Zhang | |
| 2010/0105072 A1 | 4/2010 | Kirkpatrick et al. | |
| 2011/0113496 A1 | 5/2011 | Shultz et al. | |
| 2012/0264697 A1 | 10/2012 | Liu et al. | |
| 2013/0236453 A1 * | 9/2013 | Croce | A61K 31/7088 424/133.1 |
| 2014/0234335 A1 | 8/2014 | Hori et al. | |

FOREIGN PATENT DOCUMENTS

| | | |
|---|---|---|
| WO | 99/03976 | 1/1999 |
| WO | 2004/071443 | 8/2004 |
| WO | 2012/135842 | 10/2012 |

OTHER PUBLICATIONS

D. Kong, "Echinomycin, a Small-Molecule Inhibitor of Hypoxia-Inducible Factor-1 DNA-Binding Activity", Cancer Research vol. 65, No. 19, Oct. 1, 2005, pp. 9047-9055.
Extended European Search Report, issued in European Application No. 16837853.7, dated Mar. 8, 2019.
Greenblatt, MB et al., "Graft versus Host Disease in the Bone Marrow, Liver and Thymus Humanized Mouse Model." PLoS ONE, Sep. 5, 2012, vol. 7, No. 9.

* cited by examiner

*Primary Examiner* — Kimberly Chong
(74) *Attorney, Agent, or Firm* — Michael Ye; Morris, Manning & Martin, LLP

(57) ABSTRACT

A method of preventing the development of GvHD or reducing the severity of GvHD in a mammalian subject receiving an allogeneic hematopoietic stem cell (HSC) transplant includes administering to the subject a pharmaceutical composition comprising an active agent that inhibits the biological activity or expression of hypoxia-inducible factor-1a (HIF-1a) or hypoxia-inducible factor-2a (HIF-2a), wherein the active agent is administered in an amount effective for preventing or reducing the severity GvHD in the subject.

18 Claims, 18 Drawing Sheets

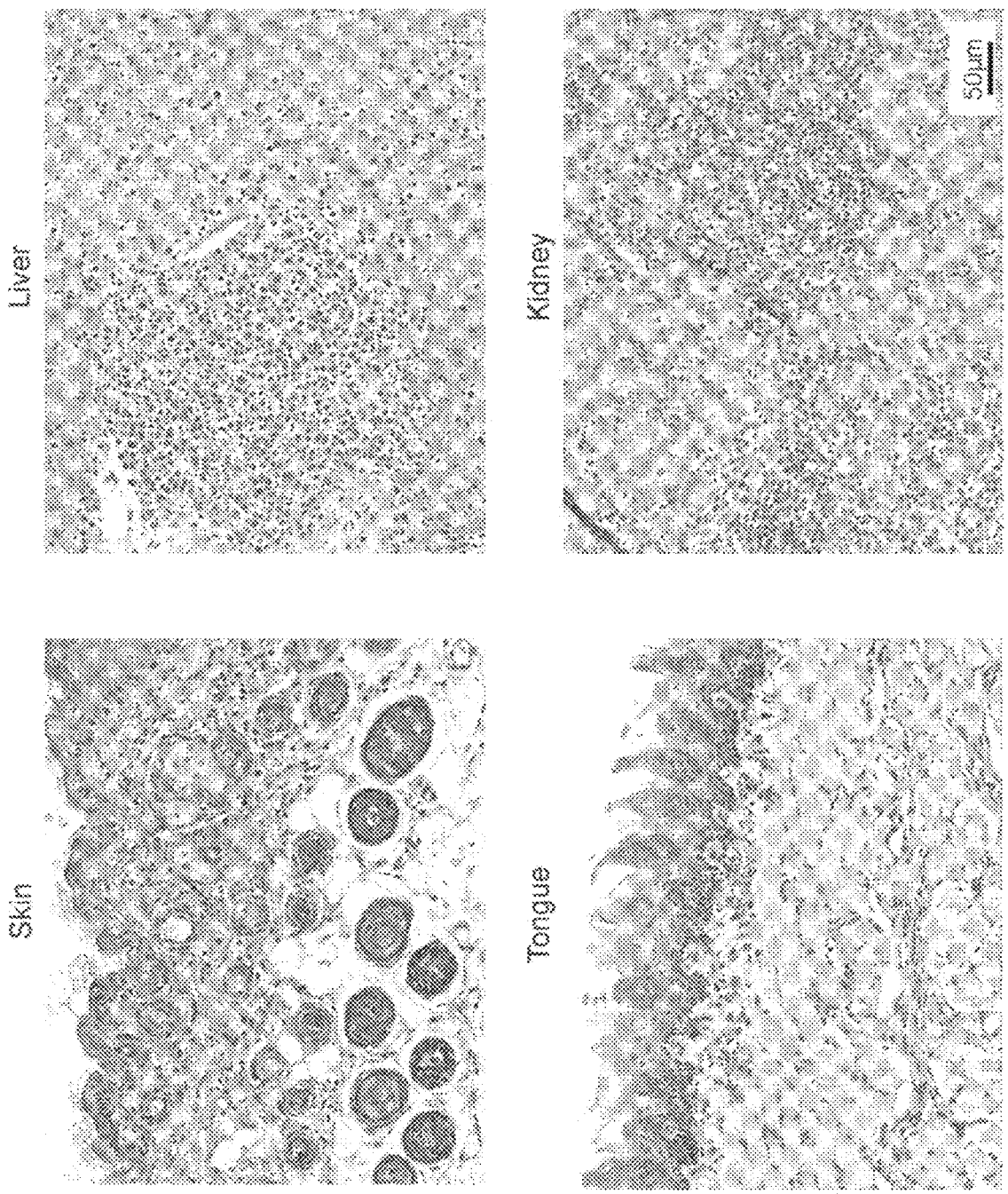

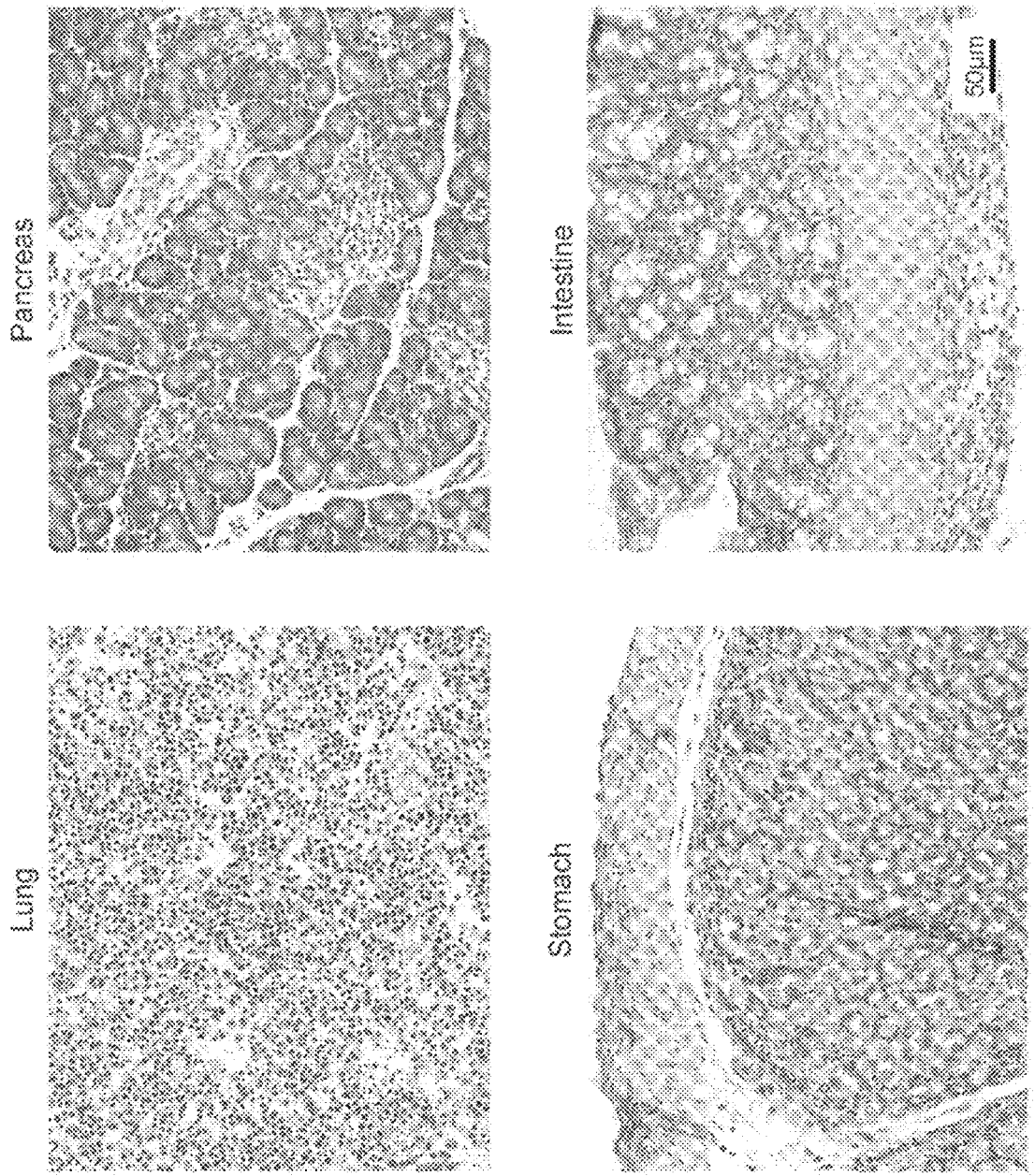
FIGURE 2A (con't)

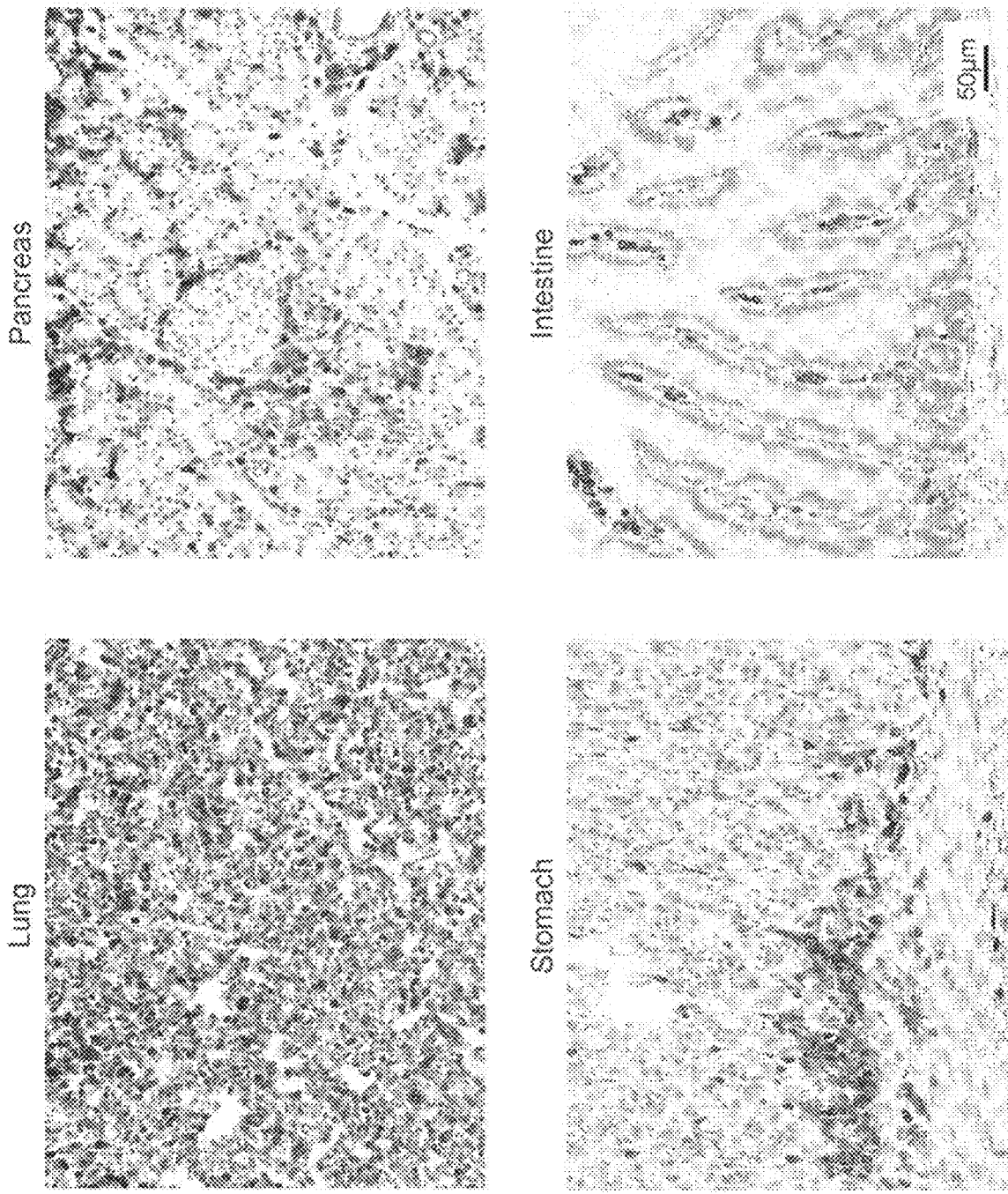
FIGURE 2B (con't)

A

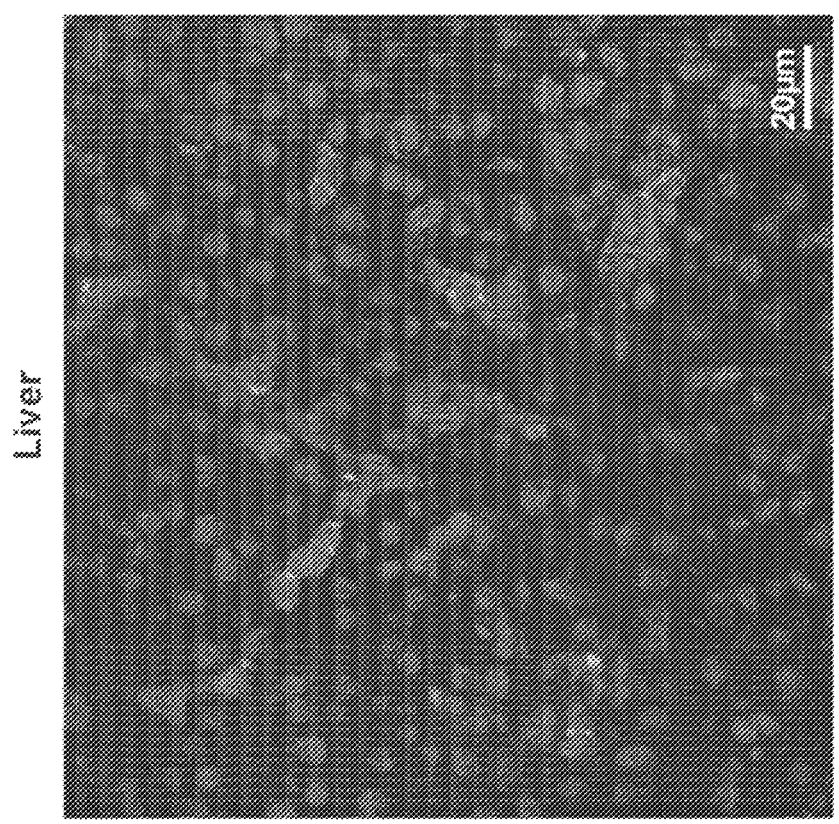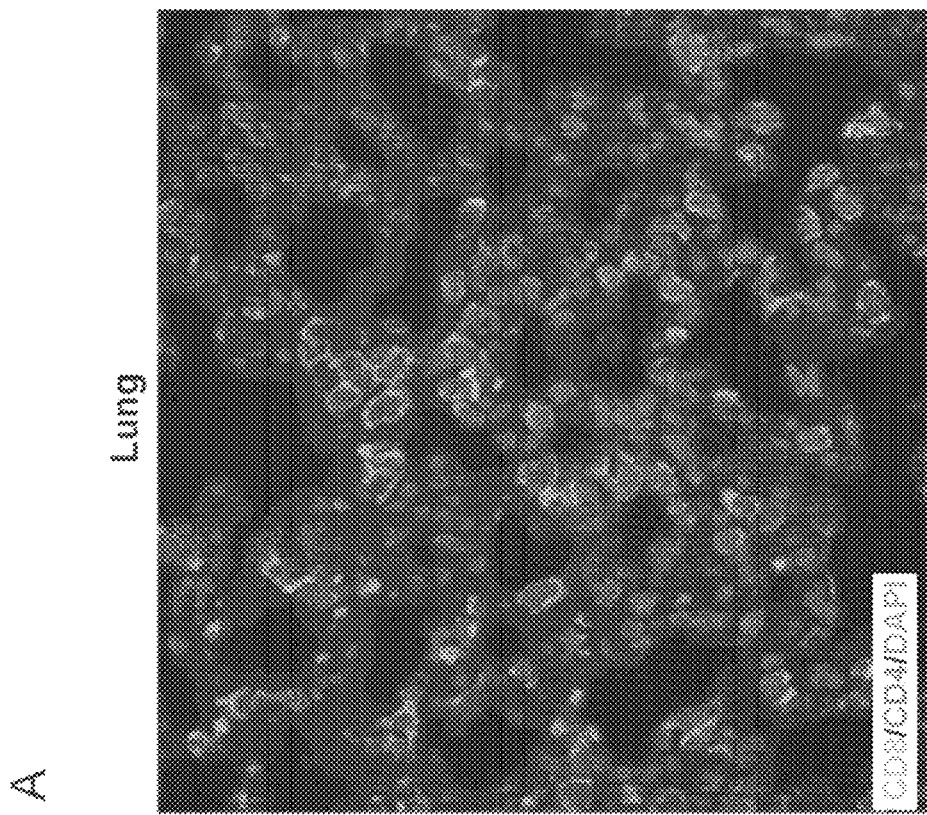
FIGURE 3A (con't)

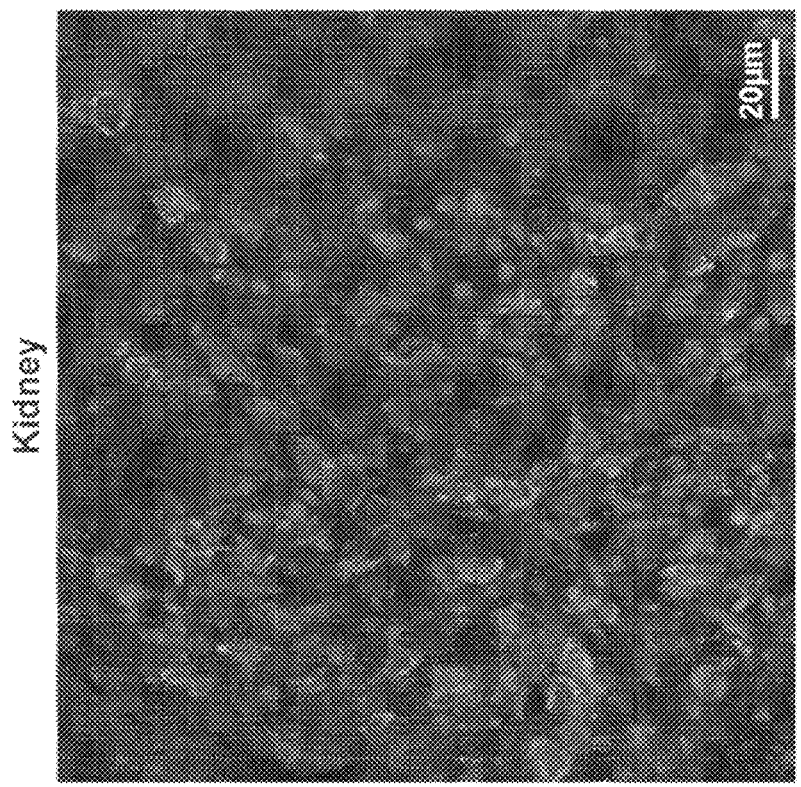
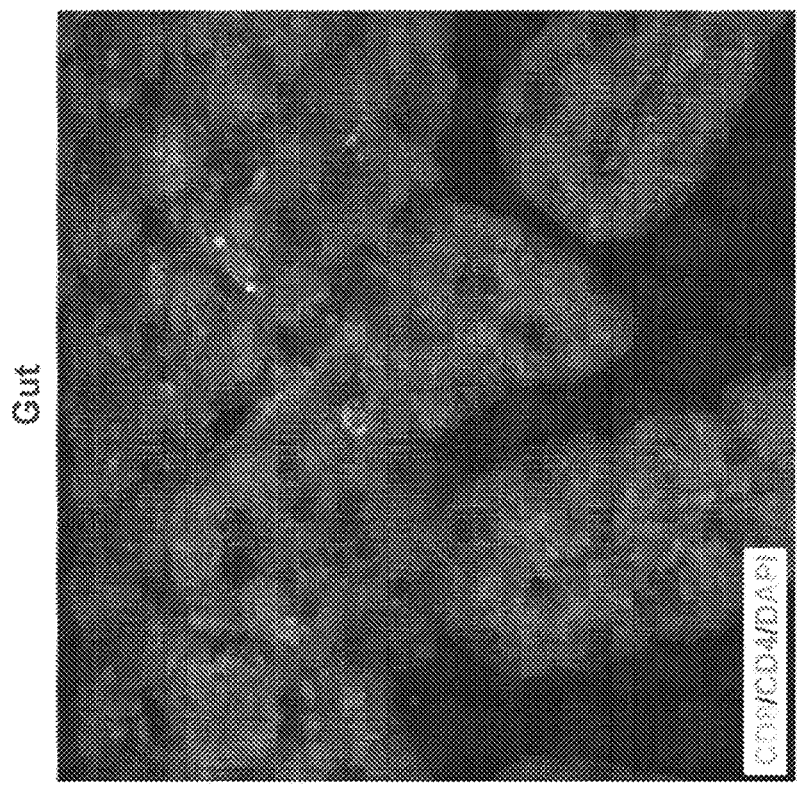
FIGURE 3A (con't)

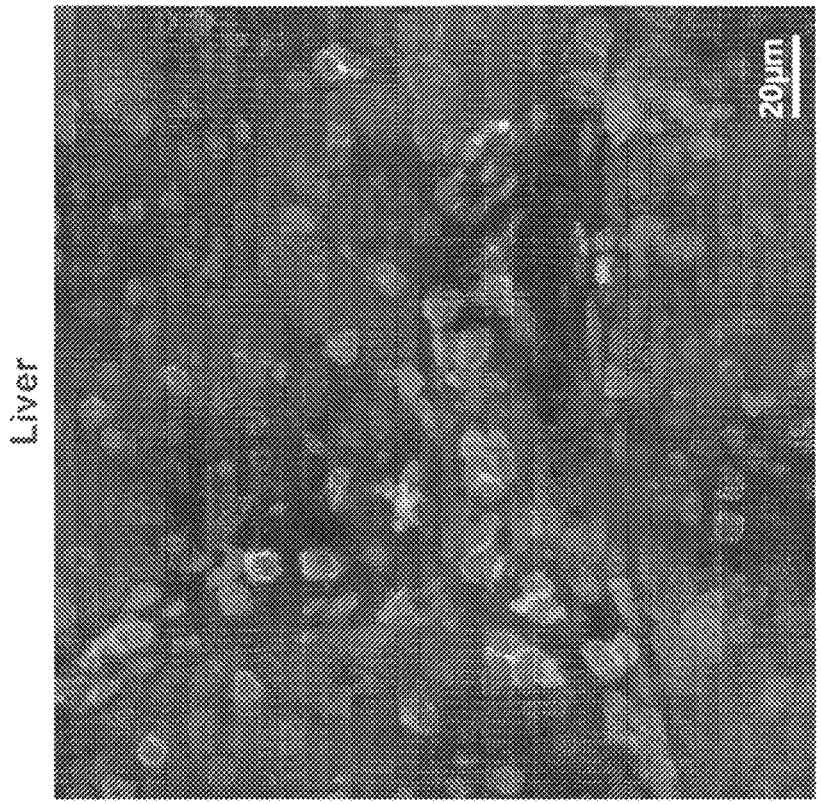
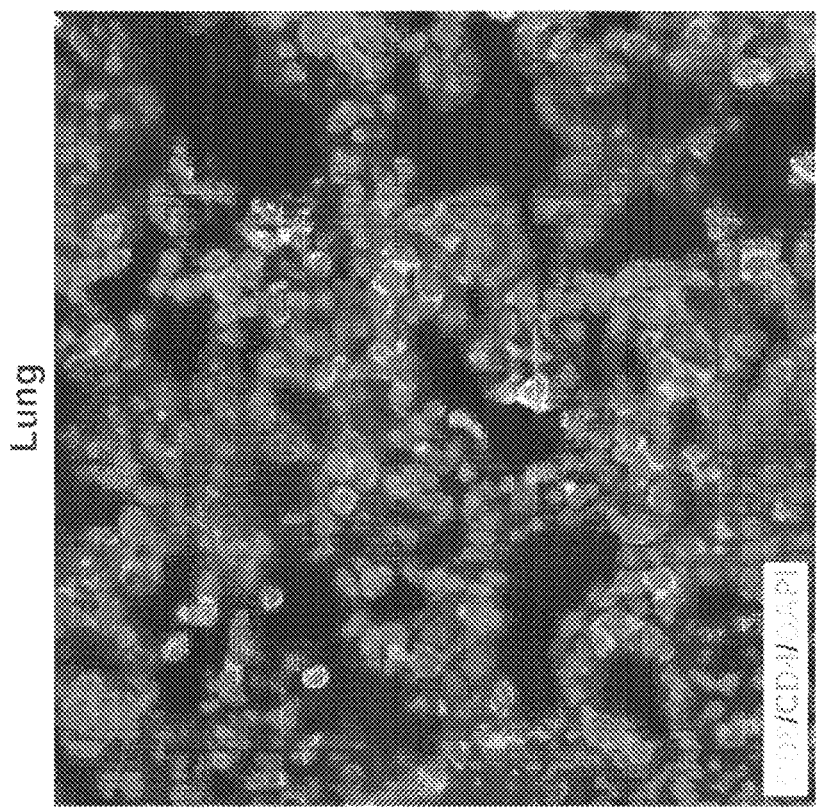
FIGURE 3B (con't)

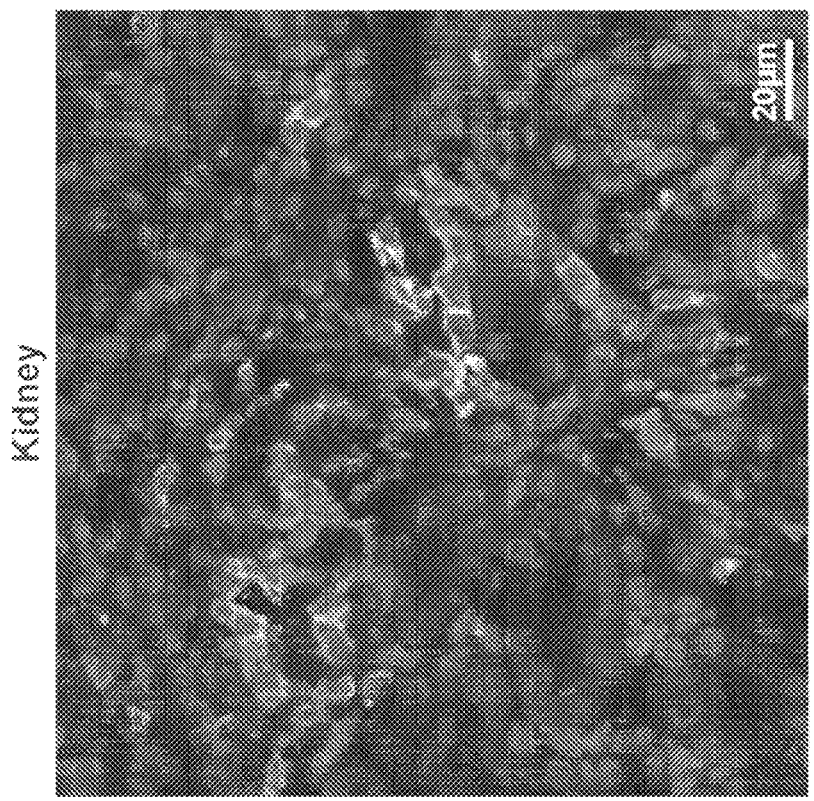
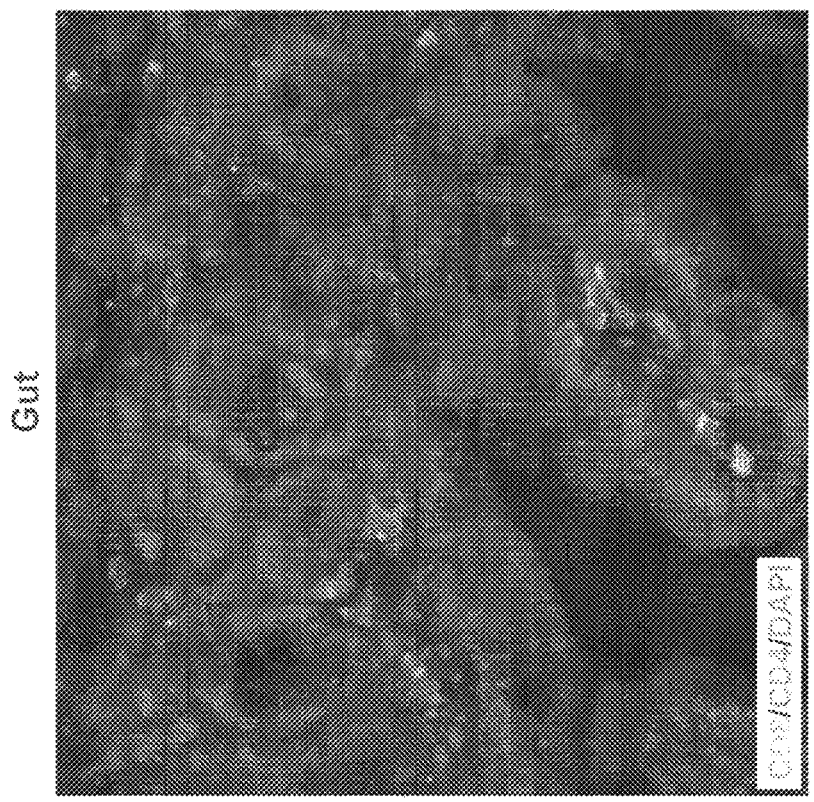
FIGURE 3B (con't)

A

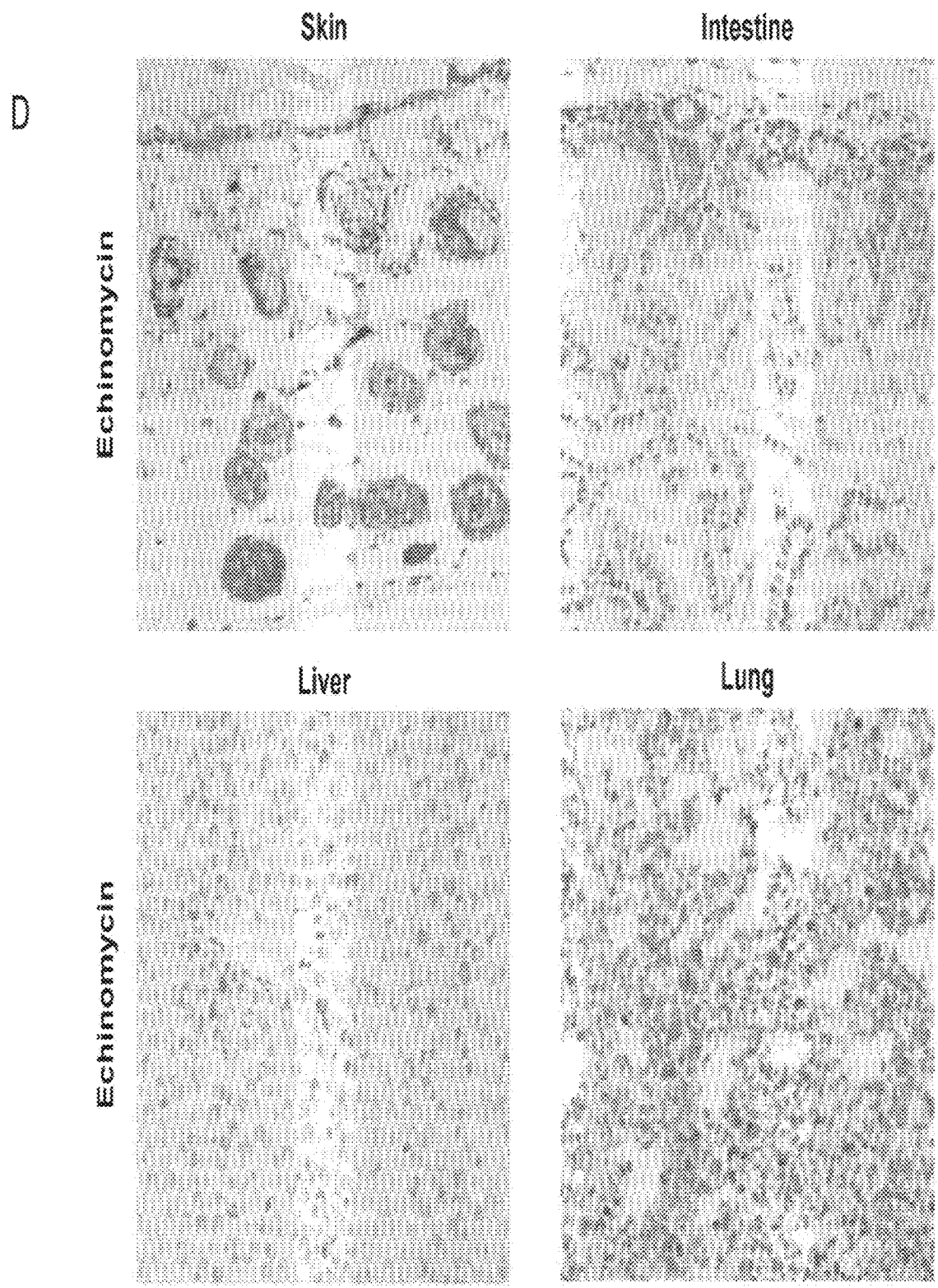
FIGURE 5D (con't)

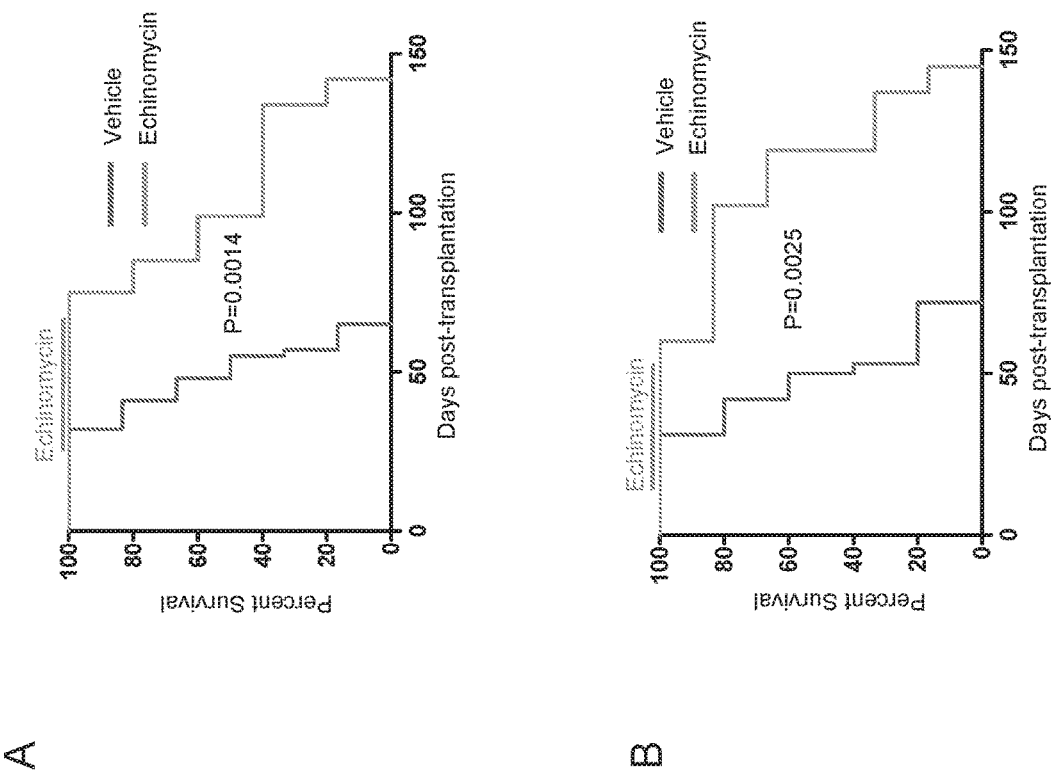

COMPOSITIONS AND METHODS FOR TREATING GRAFT VERSUS HOST DISEASE

This application claims priority to U.S. Patent Application Ser. No. 62/207,000, filed Aug. 19, 2015. The entirety of the aforementioned application is incorporated herein by reference.

FIELD

The present application relates generally to medical treatment of graft-versus-host disease ("GvHD"). More particularly, the present application relates to the use of HIF-α-inhibiting compositions for preventing the development of GvHD or reducing the severity of GvHD in a mammalian subject receiving an allogeneic hematopoietic stem cell (HSC) transplant.

BACKGROUND

Allogeneic hematopoietic stem cell transplantation (HSCT) is a potential curative therapy for hematologic malignancies. While the lymphocytes in donor bone marrow (BM) play a critical role in the prevention of tumor relapse, they are also responsible for the development of graft-versus-host disease (GvHD)(Ferrara, J L et al., Lancet, 373(9674):1550-1561 (2009). GvHD causes multi-organ damage and is one of the leading causes of morbidity and mortality associated with HSCT in patients. Despite advances in preventing GvHD in humans by the use of non-specific immunosuppressive drugs, GvHD remains a significant cause of morbidity and mortality following HSCT. Currently, there is no effective treatment for established GVHD.

Clinically, graft-versus-host-disease is divided into acute and chronic forms. The acute or fulminant form of the disease (aGvHD) is normally observed within the first 100 days post-transplant, and is a major challenge to the effectiveness of transplants owing to the associated morbidity and mortality. The chronic form of graft-versus-host-disease (cGvHD) normally occurs after 100 days. The appearance of moderate to severe cases of cGvHD adversely influences long-term survival. After bone marrow transplantation, T cells present in the graft, either as contaminants or intentionally introduced into the host, attack the tissues of the transplant recipient after perceiving host tissues as antigenically foreign. The T cells produce an excess of cytokines, including TNF alpha and interferon-gamma (IFN-γ). A wide range of host antigens can initiate graft-versus-host-disease, among them the human leukocyte antigens (HLAs). However, graft-versus-host disease can occur even when HLA-identical siblings are the donors. Classically, acute graft-versus-host-disease is characterized by selective damage to the liver, skin and mucosa, and the gastrointestinal tract. Additional studies show that that other graft-versus-host-disease target organs include the immune system (such as the bone marrow and the thymus) itself, and the lungs in the form of idiopathic pneumonitis. Chronic graft-versus-host-disease also attacks the above organs, but over its long-term course can also cause damage to the connective tissue and exocrine glands.

A clinically relevant humanized animal model is critical for the development of new strategies for the treatment of GvHD. Significant advances have been made towards generating robust models for GvHD in humanized mice, although these models are not without their drawbacks. To date, the best models take advantage of immunodeficient mice, particularly the non-obese diabetic (NOD).scid IL2rγ0 (NSG) strain, in which at least $5 \times 10^6$ human PBMC are transplanted intravenously into adult mice (Ito, R. et al., *Transplantation*, 87(11):1654-1658 (2009); King, M A et al., *Clin. Exp. Immunol.*, 157(1):104-118 (2009)). Although these models exhibit lethal GvHD, they do not fully recapitulate pathogenesis of the human disease. For example, the immune damage is notably most severe in the lung, while only mild infiltration to the skin and liver is achieved (Id.), the latter being the most common target organs in human GvHD (Jacobsohn D A et al., *Orphanet J Rare Dis.*, 2:35 (2007). Furthermore, all current models that rely either on human PBMC or T-cell purified cord blood to induce xeno-GvHD do not address the fact that human GvHD occurs following HSCT in which BM, rather than peripheral blood, is the main source of HSC. It is unclear if T cells in the BM and peripheral blood respond similarly to therapies.

In view of the foregoing, there is a need for improved treatments for addressing GvHD, including the identification of better druggable molecular targets, and development of animal models better reflecting the pathological features of human GvHD to facilitate drug discovery for GvHD.

SUMMARY

One aspect of the present application relates to a method of preventing the development of GvHD or reducing the severity of GvHD in a mammalian subject receiving an allogeneic hematopoietic stem cell (HSC) transplant. The method comprises the step of administering to the subject a pharmaceutical composition comprising an active agent that inhibits the biological activity or expression of hypoxia-inducible factor-1α (HIF-1α) and/or hypoxia-inducible factor-2α (HIF-2α), wherein the pharmaceutical composition is administered in an amount effective for preventing or reducing the severity GvHD in the subject.

Another aspect of the present application relates to a method of treating GvHD in a mammalian subject receiving an allogeneic hematopoietic stem cell (HSC) transplant. The method comprises the step of administering to the subject an effective amount of a pharmaceutical composition comprising an active agent that inhibits the biological activity or expression of HIF-1α and/or HIF-2α.

Another aspect of the present application relates to a pharmaceutical composition for preventing the development of GvHD or reducing the severity of GvHD in a mammalian subject receiving an allogeneic hematopoietic stem cell (HSC) transplant. The pharmaceutical composition comprises a first agent that inhibits the biological activity or expression of HIF-1α and/or HIF-2α, a second agent that enhance Treg activity, and a pharmaceutically acceptable carrier.

Another aspect of the present application relates to a method of identifying drug candidates for treatment of GvHD. The method comprises the steps of administering a test agent into a mouse with humanized systemic GvHD; monitoring survival and clinical manifestations of GvHD in the mouse; and identifying the test agent as a candidate drug for GvHD, if the test agent prevents or reduces the severity GvHD in the mouse compared to a mouse with humanized systemic GvHD receiving a control agent, wherein the mouse with humanized systemic GvHD is generated by transplanting human bone marrow cells into a newborn NSG mouse.

BRIEF DESCRIPTION OF THE DRAWINGS

The above and other objects and advantages of the application will be apparent upon consideration of the following detailed description, taken in conjunction with the accompanying figures and paragraphs.

FIG. 6. Echinomycin protects mice against lethal GvHD. Panel A. Newborn NSG pups were transplanted with human $5 \times 10^5$ BM cells. The mice were treated with the dosing regimen of echinomycin listed in FIG. 5, Panel A. Panel B. Newborn NSG pups were transplanted with human $3 \times 10^5$ BM cells. The mice were treated with the dosing regimen of echinomycin listed in FIG. 5, Panel A, except treatment is started at day 17 rather than day 27. Kaplan-Meier survival curve shows that recipients treated with echinomycin displayed significantly prolonged life span compared with recipients treated with vehicle. Data are representative of three independent experiments.

Figure 1:
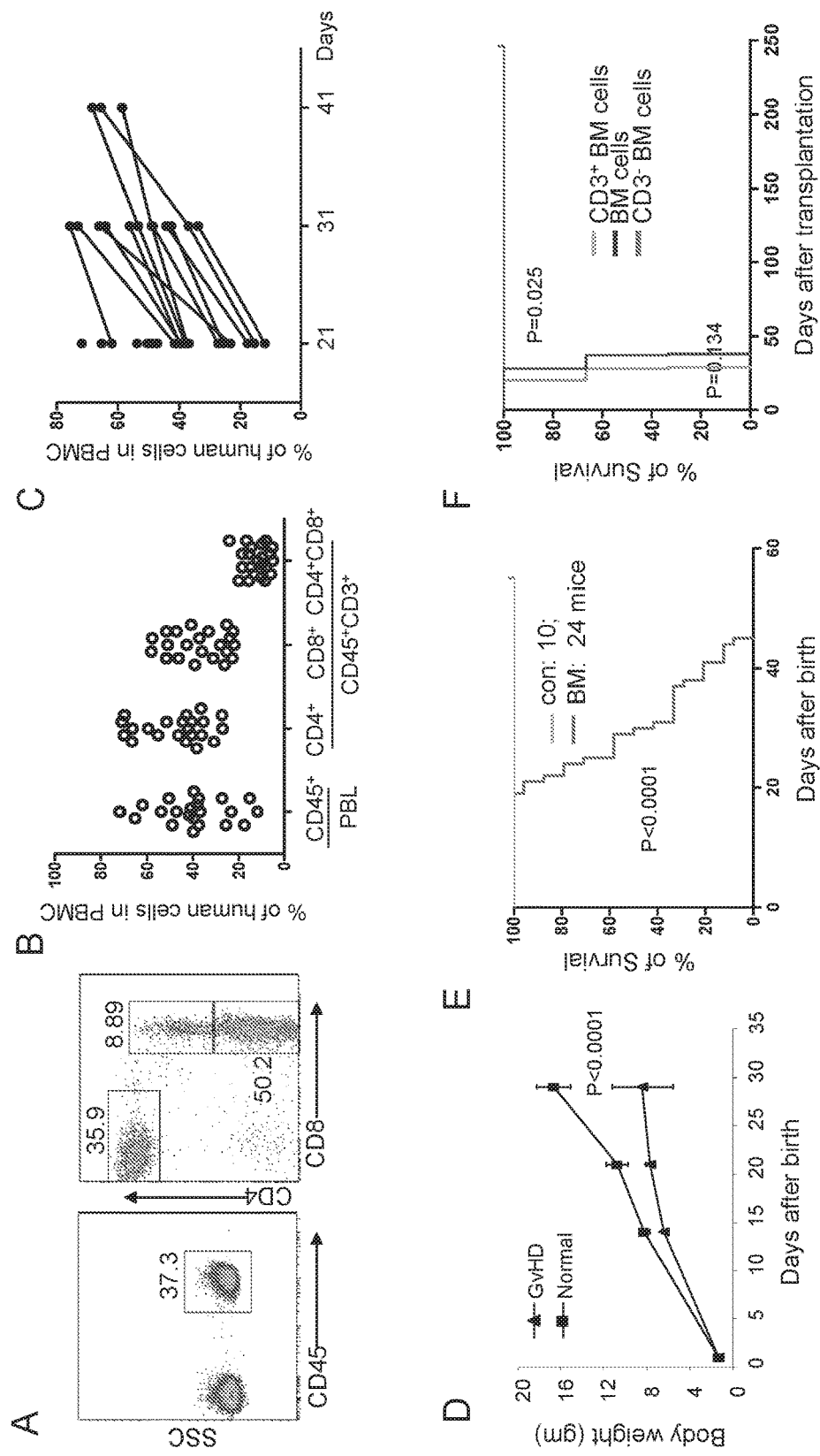
FIG. 1: *Transplantation* of human BM cells into newborn NSG mice causes acute GvHD. Newborn NSG pups irradiated with 1.3 Gys were given intrahepatic injection of $0.5 \times 10^6$ human BM cells. Panel A. Representative FACS profiles depicting distribution of human $CD45^+$, $CD4^+$, $CD8^+$, and $CD4^+CD8^+$ in PBMC of recipient at day 17 post-transplantation. Panel B. Summary of percentage of human $CD45^+$, $CD45^+CD4^+$, $CD45^+CD8^+$, and $CD45^+CD4^+CD8^+$ in PBMC of recipients at day 17 post-transplantation. Panel C. Longitudinal analysis for expansion of human cells in the NSG mice. Data shown are percentage of human $CD45^+$ cells in PBL of each recipient at days 21, 31, and 41 were measured by FACS analysis. Panel D. The bodyweight of irradiated (1.3 Gy) normal NSG mice (n=25) and those that received irradiation and intrahepatic injection of $0.5 \times 10^6$ human BM cells (GvHD, n=30) at birth. Data shown are means and SEM. Panel E. Kaplan-Meier survival curves of human BM NSG recipients transplanted with BM cells (n=24) and normal NSG mice (n=10). Mice were observed daily for survival. Control mice (green curve) received irradiation only. Panel F. Kaplan-Meier survival curves of human BM NSG recipients transplanted with human BM cells, or sorted $CD3^+$ and $CD3^-$ cells from human BM cells. Mice were observed daily for survival.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

Some modes for carrying out the present invention are presented in terms of its exemplary embodiments, herein discussed below. However, the present invention is not limited to the described embodiment and a person skilled in the art will appreciate that many other embodiments of the present invention are possible without deviating from the basic concept of the present invention, and that any such work around will also fall under scope of this application. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the enclosed paragraphs. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent or patent application publication described in this application is expressly incorporated by reference herein.

As used herein, the term "treating" means ameliorating, improving or remedying a disease, disorder, or symptom of a disease or disorder. As used herein, the phrase "preventing or reducing the severity of GvHD" refers to any symptoms reflecting a lessening of the severity of GvHD, delay in onset of GvHD, slowing of progression of GvHD, or shortening of duration of alloantibody driven GvHD, whether permanent or temporary, lasting or transient that can be attributed to administration of the hypoxia-inducible factor-1α (HIF-1α)- or hypoxia-inducible factor-2α (HIF-2α)-inhibiting composition. Additional parameters for evaluation of anti-GvHD activity may include time to neutrophil and platelet recovery, time to full donor chimerism in neutrophils, proportions of subjects with graft failure, relapse or malignancy, incidence of infections (bacterial, viral and fungal), proportions of subjects with overall survival at Day 45, at Day 100 and/or at Day 180, proportions of subjects with acute GvHD-free survival at Day 180, rates and grade of acute GvHD following administration of the HIF-α inhibitors, proportion of subjects who developed acute GvHD, and time to onset of acute GvHD. Additional secondary end points include time to engraftment and time to discharge from the hospital.

The phrase "small molecule inhibitor" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Small molecules inhibitors can be derived synthetically, semi-synthetically (i.e., from naturally occurring precursors), or biologically.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. A "progenitor cell" also has the capacity to self-renew and to differentiate into more mature cells, but is committed to a lineage (e.g., hematopoietic progenitors are committed to the blood lineage; myeloid progenitors are committed to the myeloid lineage; lymphoid progenitors are committed to the lymphoid lineage), whereas stem cells are not necessarily so limited. "Self-renewal" refers a cell with a unique capacity to produce unaltered daughter cells and therefore replenish and maintain its population numbers, and to generate specialized cell types (potency). Self-renewal can be achieved in two ways. Asymmetric cell division produces one daughter cell that is identical to the parental cell and one daughter cell that is different from the parental cell and is a more committed progenitor or differentiated cell. Symmetric cell division produces two identical daughter cells. "Proliferation" or "expansion" of cells refers to symmetrically dividing cells.

Methods of Preventing or Reducing GvHD

One aspect of the present application relates to a method of preventing the development of GvHD or reducing the severity of GvHD in a mammalian subject receiving an allogeneic hematopoietic stem cell (HSC) transplant, comprising: administering to either the subject, the transplanted HSCs, or both, a pharmaceutical composition comprising an active agent that inhibits the biological activity or expression of hypoxia-inducible factor-1α (HIF-1α) or hypoxia-inducible factor-2a (HIF-2α), wherein the active agent is administered in an amount effective for preventing or reducing the severity GvHD in the subject.

HIF-α Inhibitor Compositions

The pharmaceutical composition includes an active agent that inhibits the biological activity or expression of hypoxia-inducible factor-1α (HIF-1α), hypoxia-inducible factor-2α (HIF-2α), or both. As used herein, the term "HIF-α" is used with reference to HIF-1α, HIF-2α, or both. HIF-1 and HIF-2 are transcription factors found in mammalian cells cultured under reduced oxygen tension that play an essential role in cellular and systemic homeostatic responses to hypoxia. HIF-1 and HIF-2 are each composed of a heterodimer composed of a 120-kD HIF-1α or HIF-2α subunit complexed with a common 91- to 94-kD HIF-1 β subunit.

1. Small Molecule HIF-α Inhibitors.

In one embodiment, the active agent is a small molecule inhibitor of HIF-1α or HIF-2α. Exemplary small molecule inhibitors of HIF-1α or HIF-2α include, but are not limited to, polyamides, such as echinomycin, which inhibit the interaction between HIF and DNA; inhibitors of the interaction between HIF-α and p300, such as chetomin, eudistidine A, KCN1, HBS1, Quinone 1, Compound 3 and OHM1 as described in Wilkins et al., ChemMedChem, 11:773-786 (2016); inhibitors and modulators of HIF dimerization, such as acriflavine, a combination of trypaflavine and proflavine, cyclo-CLLFVY, and 0X3 (also described in Wilkins); YC-1 (3-(5'-hydroxymethyl-2'-furyl)-1-benzylindazole); quinocarmycin monocitrate (KW2152) and its hydrocyanization product DX-52-1 (NSC-607097); NSC-259968; NSC-259969; NCGC00043898, NCGC00044926, NCGC00049606, and NCGC00056044, as described in Xia et al., *Mol. Cancer*, 8:117 (2009); topoisomerase I inhibitors, such as camptothecin (NSC-606985) and camptothecin analogues, such as topotecan (NSC-609699), NSC-639174, camptothecin-11 (CPT-11; Camptosar, irinotecan), which yields the yields the active moiety, SN38 (10-hydroxy-7-ethyl-camptothecin) upon hydrolysis by carboxylesterase 2, and EZN-2208, a pegylated-SN38 drug conjugate; topoisomerase II inhibitors, such as daunorubicin, and mitoxantrone; heat shock protein-90 inhibitors, such as geldanamycin, 17-allylamino-17-demethoxygeldanamycin (17-AAG) and 17-dimethylaminoethylamino-17-demethoxy-geldanamycin (17-DMAG), as well as oxime derivatives of radicicol, such as KF58333; microtubule disrupting agents, such as taxotere, 2-methoxyestradiol (2-MeOE2), vincristine, discodermolide, and epothilone B; thioredoxin inhibitors, such as PX-12 (1-methylpropyl 2-imidazolyl disulfide) and Pleurotin; mTOR inhibitors, such as rapamycin, CCI-779, and Rad001; histone deacetylase inhibitors, such as romidepsin (FK228, FR901228, NSC 630176); and PI3-kinase inhibitors, such as wortmanin and LY294002; digoxin and their analogues, PX-478 (S-2-amino-3-[4V-N,N-bis(2-chloroethyl)amino]-phenyl propionic acid N-oxide dihydrochloride), PX-478 2HCl; manassantin A and its analogs, MA04, MA07, and MA11 as described in Kwon et al., *J. Med. Chem.*, 58 (19):7659-7671 (2015); and BAY 87-2243.

2. RNA Inhibitors of HIF-α.

In some embodiments, the active agent is an antisense RNA or an siRNA directed against HIF-1α or HIF-2α. EZN-2968 is an exemplary antisense oligonucleotide inhibitor of HIF-1α.

In one embodiment, the antisense oligonucleotide or polynucleotide comprises a single stranded antisense oligonucleotide or polynucleotide targeting for degradation. In certain embodiments, the HIF-1α inhibitor is a single stranded antisense oligonucleotide complementary to a HIF-1α or HIF-2α mRNA sequence. The single stranded antisense oligonucleotide or polynucleotide may be synthetically produced or it may be expressed from a suitable expression vector. The antisense nucleic acid is designed to bind via complementary binding to the mRNA sense strand so as to promote RNase H activity, which leads to degradation of the mRNA. Preferably, the antisense oligonucleotide is chemically or structurally modified to promote nuclease stability and/or increased binding.

In certain embodiments, the antisense oligonucleotide may be modified to produce an oligonucleotide with non-conventional chemical or backbone additions or substitutions, including but not limited to peptide nucleic acids (PNAs), locked nucleic acids (LNAs), morpholino backboned nucleic acids, methylphosphonates, duplex stabilizing stilbene or pyrenyl caps, phosphorothioates, phosphoroamidates, phosphotriesters, and the like. By way of example, the modified oligonucleotides may incorporate or substitute one or more of the naturally occurring nucleotides with an analog; internucleotide modifications incorporating, for example, uncharged linkages (e.g., methyl phosphonates, phosphotriesters, phosphoamidates, carbamates, etc.) or charged linkages (e.g., phosphorothioates, phosphorodithioates, etc.); modifications incorporating intercalators (e.g., acridine, psoralen, etc.), chelators (e.g., metals, radioactive metals, boron, oxidative metals, etc.), or alkylators, and/or modified linkages (e.g., alpha anomeric nucleic acids, etc.).

An siRNA is a double-stranded RNA that can be engineered to induce sequence-specific post-transcriptional gene silencing of mRNAs. Synthetically produced siRNAs structurally mimic the types of siRNAs normally processed in cells by the enzyme Dicer. When expressed from an expression vector, the expression vector is engineered to transcribe a short double-stranded hairpin-like RNA (shRNA) that is processed into a targeted siRNA inside the cell. Synthetic siRNAs and shRNAs may be designed using well known algorithms and synthesized using a conventional DNA/RNA synthesizer. Kits for the production of vectors comprising shRNAs are available, such as, for example, Imgenex's GENESUPPRESSOR™ Construction Kits and Invitrogen's BLOCK-IT™ inducible RNAi plasmid and lentivirus vectors.

In some cases, the siRNAs may be synthesized as a locked nucleic acid (LNA)-modified siRNA. An LNA is a nucleotide analogue that contains a methylene bridge connecting the 2'-oxygen of the ribose with the 4' carbon. The bicyclic structure locks the furanose ring of the LNA molecule in a 3'-endo conformation, thereby structurally mimicking the standard RNA monomers.

3. Gene Editing Compositions.

In other embodiments, the active agent includes one or more vectors encoding a gene editing system engineered to reduce, prevent or otherwise disrupt endogenous expression of HIF-1α or HIF-2α. In one embodiment, the gene editing system includes a nuclease for facilitating stable, site-specific recombination in a recipient host. Exemplary nucleases in accordance with these embodiments includes a Clustered Regularly Interspaced Short Palindromic Repeats (CRISPR)-associated (Cas) protein, a zinc finger nuclease (ZFN), a Transcription Activator-Like Effector Nuclease (TALEN), or a meganuclease.

In some embodiments, a CRISPR/Cas system is utilized to induce a single or a double strand break in the target cell's genome. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, e.g., Cong, *Science*, 15:339(6121):819-823 (2013) and Jinek et al., *Science*, 337(6096):816-21 (2012)). By transfecting a cell with the required elements including a Cas gene and specifically designed CRISPRs, the organism's genome can be cut and modified at any desired location. Methods of preparing compositions for use in genome editing using the CRISPR/Cas systems are described in U.S. Pat. No. 8,697,359 and US 2014-0068797.

In general, the "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong et al. and Jinek et al. above, A single fused crRNA-tracrRNA construct can also be referred to as a guide RNA or gRNA (or single-guide RNA (sgRNA)). Within an sgRNA, the crRNA portion can be identified as the "target sequence" and the tracrRNA is often referred to as the "scaffold".

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. In certain preferred embodiments, the CRISPR system is used to target a DNA sequence by inserting a short DNA fragment containing the target sequence into a guide RNA expression plasmid. A suitable sgRNA expression plasmid may contain the target sequence (about 20 nucleotides), a form of the tracrRNA sequence (the scaffold) as well as a suitable promoter and necessary elements for proper processing in eukaryotic cells. Such vectors are commercially available (see, e.g., Addgene, a plasmid repository in Cambridge, Mass.). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

In some embodiments, a zinc finger nuclease (ZFN) may be used to induce a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe (sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

The most common cleavage domain is the Type IIS enzyme Fok1. Fok1 catalyzes double-stranded cleavage of DNA, at 9 nucleotides from its recognition site on one strand and 13 nucleotides from its recognition site on the other. One or more of these enzymes (or enzymatically functional fragments thereof) can be used as a source of cleavage domains.

In other embodiments, a transcription activator-like effector nuclease (TALEN) is used to the element that induces a single or a double strand break in the target cell's genome. TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats. Methods of engineering TAL to bind to specific nucleic acids are described in U.S. Pat. No. 8,586,363.

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Typically, the genome editing composition includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc. Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc.

A polynucleotide for site-specific recombination includes a suitable donor sequence. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

The expression vector for expressing an siRNA, CRISPR-cas or other gene editing component(s) may be a viral vector or a non-viral vector. Viral vectors may be derived from a retrovirus (including a lentivirus, such as HIV-1 and HIV-2), adeno-associated virus (AAV), adenovirus, herpesvirus, vaccinia virus, poliovirus, poxvirus, Sindbis virus, other RNA viruses, including alphaviruses, astroviruses, coronaviruses, paramyxoviruses, orthomyxoviruses, picornaviruses, and togaviruses; other DNA viruses, including papovaviruses and parvoviruses, and the like. A non-viral vector is simply a "naked" expression vector that is not packaged with virally derived components (e.g., capsids and/or envelopes).

In certain cases, these vectors may be engineered to target specific cell populations, such as $CD34^+$ cells, by utilizing targeting characteristics inherent to the virus vector or by engineering targeting characteristics into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

Non-viral expression vectors can be utilized for non-viral gene transfer, either by direct injection of naked DNA or by encapsulating the polynucleotides or expression vectors in liposomes, microparticles, microcapsules, virus-like particles, or erythrocyte ghosts. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

Sources of Allogeneic Stem Cells

In one embodiment, the source of allogeneic hematopoietic stem cells (HSCs) is selected from the group consisting of bone marrow, peripheral blood and umbilical cord blood. In another embodiment, the source of HSCs comprises embryonic stem cells (ESCs) or induced pluripotent stem cells (iPCs). In some embodiment, mesenchymal stromal cells were co-transplanted in the recipient with the HSCs.

Stem cells or stem cell sources for use in the present methods include bone marrow, peripheral blood, umbilical cord blood, hematopoietic stem cells (HSCs), mesenchymal stem cells (MSCs), embryonic stem cells (ESCs), and induced pluripotent stem cells (iPSCs). Methods for extracting, isolating and purifying HSCs are well known in the art.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art. When transplanted into lethally irradiated animals or humans, hematopoietic stem cells can repopulate the erythroid, neutrophil-macrophage, megakaryocyte and lymphoid hematopoietic cell pool.

HSCs may be identified according to certain phenotypic or genotypic markers. For example, HSCs may be identified by their small size, lack of lineage (lin) markers, low staining (side population) with vital dyes such as rhodamine 123 (rhodamineDULL, also called rholo) or Hoechst 33342, and presence of various antigenic markers on their surface, many of which belong to the cluster of differentiation series (e.g., CD34, CD38, CD90, CD133, CD105, CD45, and c-kit, the receptor for stem cell factor). HSCs are mainly negative for the markers that are typically used to detect lineage commitment, and, thus, are often referred to as Lin(−) cells. Most human HSCs may be characterized as $CD34^+$, $CD59^+$, $Thy1/CD90^+$, $CD38^{lo/−}$, $C-kit/CD117^+$, and Lin (−). However, not all stem cells are covered by these combinations, as certain HSCs are $CD34^−/CD38^−$. Also some studies suggest that earliest stem cells may lack c-kit on the cell surface. For human HSCs, CD133 may represent an early marker, as both $CD34^+$ and $CD34^−$ HSCs have been shown to be $CD133^+$. It is known in the art that $CD34^+$ and Lin(−) cells also include hematopoietic progenitor cells.

Suitable sources of hematopoietic stem and progenitor cells for use in the methods of the present application include, but are not limited to, cells isolated or obtained from an organ of the body containing cells of hematopoietic origin. By "isolated" is meant material that is removed from its original environment. For example, a cell is isolated if it is separated from some or all of the components that normally accompany it in its native state. For example, an "isolated population of cells," an "isolated source of cells," or "isolated hematopoietic stem and progenitor cells" and the like, as used herein, refer to in vitro or ex vivo separation of one or more cells from their natural cellular environment, and from association with other components of the tissue or organ, i.e., it is not significantly associated with in vivo substances.

Hematopoietic stem and progenitor cells for use in the methods of the present application may be depleted of mature hematopoietic cells such as T cells, B cells, NK cells, dendritic cells, monocytes, granulocytes, erythroid cells, and their committed precursors from bone marrow aspirate, umbilical cord blood, or mobilized peripheral blood (mobilized leukapheresis product). Mature, lineage committed cells are depleted by immunodepletion, for example, by labeling solid substrates with antibodies that bind to a panel of so-called "lineage" antigens: CD2, CD3, CD11b, CD14, CD15, CD16, CD19, CD56, CD123, and CD235a. A subsequent step can be performed to further purify the population of cells, in which a substrate labeled with antibodies that bind to the CD34+ antigen are used to isolate primitive hematopoietic stem and progenitor cells. Kits are commercially available for purifying hematopoietic stem and progenitor cells from various cell sources and in particular embodiments, these kits are suitable for use with the methods of the present application. Exemplary commercially available kits for purifying hematopoietic stem and progenitor cells include, but are not limited to Lineage (Lin) Depletion Kit (Miltenyi Biotec); CD34+ enrichment kit (Miltenyi Biotec); and RosettaSep (Stem Cell Technologies).

Embryonic stem (ES) cells are used for investigating early developmental events and provide a promising source of tissues potentially useful for regenerative therapies. Recent breakthroughs in generating iPSCs provide alternative means to obtain ES-like cells without destroying embryos. iPS cells are known to share numerous traits with ES cells, such as colony morphology, transcriptome, self-renewal ability and pluripotency.

iPSCs may be generated by introducing a plurality of reprogramming factors (Oct3/4, Sox2, and Klf4/c-Myc or Nanog/Lin28) into somatic cells. In particular, one or more nuclear reprogramming factors may be used to induce reprogramming of a differentiated cell, such as a somatic cell, without using eggs, embryos, or ES cells. Efficiency of the induction process is enhanced by utilizing an agent that antagonizes a cell specific gene or upregulates expression or activity of a nuclear reprogramming gene during the induction process. Reprogramming of a differentiated cell provides a convenient and highly reproducibly means for establishing a population of iPSCs having pluripotency and growth ability similar to those of ES cells.

In some embodiments, the nuclear reprogramming factor may be introduced into a cell by transducing the cell with a recombinant vector comprising a gene encoding the nuclear reprogramming factor along with along with the agent. Accordingly, the cell can express the nuclear reprogramming factor expressed as a product of a gene contained in the recombinant vector. The agent acts to antagonize a cell specific gene or upregulate expression or activity of a nuclear reprogramming gene during the induction process to induce reprogramming of a differentiated cell at an increased efficiency rate as compare to use of the nuclear reprogramming factor alone. The agent may also substitute for a specific nuclear reprogramming factor, for example, Sox2.

Somatic cells for creating iPSCs may be primary cells or immortalized cells. Such cells may be primary cells (non-immortalized cells), such as those freshly isolated from an animal, or may be derived from a cell line (immortalized cells). In preferred embodiments, the somatic cells are mammalian cells, such as, for example, human cells or mouse cells. They may be obtained by well-known methods, from different organs, such as, but not limited to skin, lung, pancreas, liver, stomach, intestine, heart, reproductive organs, bladder, kidney, urethra and other urinary organs, or generally from any organ or tissue containing living somatic cells. Mammalian somatic cells include, by way of example, adult stem cells, sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. In particular embodiments, fibroblasts are used. The term "somatic cell", as used herein, is also intended to include adult stem cells. An adult stem cell is a cell that is capable of giving rise to all cell types of a particular tissue. Adult stem cells include cells such as, hematopoietic stem cells, neural stem cells, and mesenchymal stem cells.

The nuclear reprogramming factors are genes, such as nuclear reprogramming genes, that induce pluripotency and are utilized to reprogram differentiated or semi-differentiated cells to a phenotype that is more primitive than that of the initial cell, such as the phenotype of a PSC. Such genes are utilized with agents determined to antagonize a somatic cell specific gene or upregulate expression or activity of a nuclear reprogramming gene to increase induction efficiency. Such genes and agents are capable of generating a PSC from a somatic cell upon expression of one or more such genes having been integrated into the genome of the somatic cell. As used herein, a gene that induces pluripotency is intended to refer to a gene that is associated with pluripotency and capable of generating a less differentiated cell, such as a PSC from a somatic cell upon integration and expression of the gene. The expression of a pluripotency gene is typically restricted to PSCs, and is crucial for the functional identity of PSCs.

Agents capable of antagonizing a cell specific gene or upregulating expression or activity of a nuclear reprogramming gene can include a variety of different types of molecules. An agent or candidate agent useful in any method of the present application can be any type of molecule, for example, a polynucleotide, a peptide, a peptidomimetic, peptoids such as vinylogous peptides, chemical compounds, such as organic molecules or small organic molecules, or the like. The antagonizing agent may be a polynucleotide, such as an antisense oligonucleotide or RNA molecule, such as a microRNA, dsRNA, siRNA, stRNA or shRNA.

Several genes have been found to be associated with pluripotency and may be considered nuclear reprogramming genes or factors and thus suitable for establishing a population of iPSCs for use in the methods described herein. Such genes are known in the art and include, by way of example, SOX family genes (SOX1, SOX2, SOX3, SOX15, SOX18), KLF family genes (KLF1, KLF2, KLF4, KLF5), MYC family genes (C-MYC, L-MYC, N-MYC), SALL4, OCT4, NANOG, LIN28, STELLA, NOBOX or a STAT family gene. STAT family members may include for example STAT1, STAT2, STAT3, STAT4, STAT5 (STAT5A and STAT5B), and STAT6. While in some instances, use of only one gene to induce pluripotency may be possible, in general, expression of more than one gene is required to induce pluripotency. The number of required pluripotency genes is also expected to depend on the agent or agents that are utilized in combination with the nuclear reprogramming gene, since certain agent have been determined to substitute for reprogramming genes. For example, Sox2 may be replaced with OHTM and/or nabumetone. As such, one, two, three, four or more genes may be simultaneously integrated into the somatic cell genome as a polycistronic construct to allow simultaneous expression of such genes. In certain embodiments, up to four genes are utilized to induce pluripotency including any combination of OCT3/4, Sox2, Klf4 and c-MYC. Additional reprogramming factors and methods suitable for inducing pluripotency of stem cells are disclosed in U.S. Pat. Nos. 7,682,828, 8,278,104, and U.S.

Patent Publication Nos. US 2009/0227032, US 2012/0213746, US 2013/0259842, US 2013/0323782, US 2014/0093486, US 2014/0356455, and US 2016-0145642.

In some embodiments, the HSCs are treated with one or more agents prior to transplantation into the subject. In some embodiments, the one or more agents comprise agents that inhibits the biological activity or expression of HIF-1α or HIF-2α.

In some embodiments, a subject may be transplanted with a universal iPSC donor cell line, such as an HLA-universal induced pluripotent stem cell (iPSC) line that has been engineered to silence the expression of HLA class I genes and/or HIF-α. Silencing of genes for creation of universal iPSC donor cells may be carried out using suitable nucleases, including the CRISPR-Cas system as further described above.

In some embodiments, the subject has additionally received a mesenchymal stromal cell (MSC) transplant, along with the HSCTs described herein above. MSCs exhibit immunosuppressive, regenerative and HSC-supportive properties. In particular, MSCs can provide survival signals for incoming and residing hematopoietic stem and progenitor cells (HSPCs) within the bone barrow and provide osteoblastic progenitor cells for replenishing the endosteal bone marrow niche space. There doesn't seem to be anything here regarding the method i.e. you would extract the cell, purify as necessary, treat with the appropriate agent and administer to the subject, presumably within a reasonable period of time Diseases for Treatment The HIF-α-inhibiting compositions described herein may be used alone or in combination with a source of HSCs to treat a variety of diseases in mammalian subjects. As used herein, the term "mammalian subject" refers to any animal classified as a mammal, including humans, domestic and farm animals, and zoo, sports, or pet animals, such as dogs, cats, cattle, horses, sheep, pigs, rats, mice, rabbits, etc. Preferably, the mammal is human.

In one embodiment, the subject is afflicted with leukemia and is treated with HSCs and an HIF-α-inhibiting composition described herein. As used herein, the term "leukemia" refers to progressive, malignant diseases of the blood-forming organs and is generally characterized by a distorted proliferation and development of leukocytes and their precursors in the blood and bone marrow. Exemplary leukemias for treatment include, for example, acute nonlymphocytic leukemia, chronic lymphocytic leukemia, acute granulocytic leukemia, chronic granulocytic leukemia, acute promyelocytic leukemia, large granular lymphocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

In some embodiments, the subject is afflicted with myelodysplastic syndrome (MDS) and/or any other relevant diseases.

In other embodiments, the subject is afflicted with a non-hematopoietic disease and is the recipient of embryonic stem cells (ESCs) or induced pluripotent stem cells (iPSCs). Like HSCs, these cells include progenitor cells for T cells that can induce GvHD. In some embodiments, the transplanted ESCs or iPSCs are genetically modified to reduce or eliminate expression of HIF-α therefrom. Exemplary diseases for treatment with ESCs or iPSCs in combination with an HIF-α-inhibiting pharmaceutical composition include, but are not limited to, cancers, including cancers of the blood, brain, bladder, breast, cervix, colon, head and neck, kidney, lung, non-small cell lung, mesothelioma, ovary, prostate, stomach, and uterus; liver diseases, such as liver fibrosis, hepatocellular carcinoma, liver cirrhosis and hepatitis; diabetes; degenerative diseases, such as Parkinson's disease, Alzheimer's dementia, Huntington's chorea, amyotrophic lateral sclerosis, spinal muscular atrophy, macular degeneration, retinal ischemia, and muscular dystrophy; ischemic heart disease; stroke; skeletal/bone diseases, such as osteoarthritis, osteochondral disease, rheumatoid arthritis, osteoporosis, juvenile osteoporosis, bone loss due to rheumatoid arthritis, inflammatory arthritis, osteomyelitis, corticosteroid treatment, bone loss, degenerative joint disease, cartilage degeneration, herniation, rupture and/or degenerative diseases of the intervertebral disc, injuries and diseases of ligament, tendon, synovial capsule, synovial membrane and meniscal tissues, bone fractures and bone defects.

Administration of HSCs

The effective dose of HSCs per injection for use in conjunction with HIF-α inhibitors for preventing or reducing the severity of GvHD may be between 1 cells/kg body weight and $1 \times 10^6$ cells/kg body weight; between 2 cells/kg body weight and $1 \times 10^6$ cells/kg body weight; between 2.5 cells/kg body weight and $1 \times 10^6$ cells/kg body weight; between 2 cells/kg body weight and $1 \times 10^5$ cells/kg body weight; between 2.5/kg body weight and $1 \times 10^5$ cells/kg body weight; between 2 cells/kg body weight and $3 \times 10^4$ cells/kg body weight; between 2.5 cells/kg body weight and $3 \times 10^4$ cells/kg body weight; between $2 \times 10^4$ cells/kg body weight and $2 \times 10^6$ cells/kg body weight; between 2.5×cells/kg body weight and $2 \times 10^4$ cells/kg body weight; between 2.5 cells/kg body weight and $1 \times 10^4$ cells/kg body weight; between 2 cells/kg body weight and $1 \times 10^3$ cells/kg body weight; or between 2.5 cells/kg body weight and $1 \times 10^3$ cells/kg body weight.

The HSCs can be administered by intravenous injection, arterial injection, selectable arterial injection, intramuscular injection, intraperitoneal injection, intracerebral injection, intradermal injection or bone marrow injection.

Preferably, the subject is "conditioned" prior to administration of the HSCs. As used herein the term "conditioning" or "conditioned" in the context of a patient pretreatment prior to HSCT typically means destroying substantially the bone marrow and immune system by a suitable procedure, such as reduced intensity conditioning (MC) or myeloablative conditioning. RIC includes, for example, treatment with a chemotherapeutic agent, such as fludarabine, typically at 30 mg/m²/day for three days followed by total body irradiation (TBI) typically at 1×200 cGy/day. Myeloablative conditioning involves high dose chemotherapy and total body irradiation (TBI), typically performed according to national guidelines adapted to institutional practices, and includes the administration of a suitable chemotherapeutic agent. TBI may be carried out with an irradiation dose of 0.5-10 Grey. Suitable chemotherapeutic agents for conditioning include, but are not limited to, fludarabine, busulphan, cyclophosphamide, methotrexate, cyclosporin, and combinations thereof. TBI will typically occur from approximately days 8 to 10 (days −8 and −1 relative to HSCT). In one embodiment, the TBI dose is 200 cGy given twice daily for a total dose of 1200 cGy.

Exemplary dosing regimens conditioning include, for example: (1) Fludarabin at 25 mg/m$^2$/day i.v.×3 days (for approximately 2-3 days) for a total dose of 75 mg/m$^2$; (2) Busulphan at 0.8 mg/kg/6 h (for approximately 2 to 4 days); (3) Cyclophosphamide at 60 mg/kg/×2 days (approximately for 2 days) for a total dose of 120 mg/kg. To reduce the risk of CYC-induced hemorrhagic cystitis, patients may also receive high volume fluid flushes and mesna.

Administration of HIF-α Inhibitors

Inhibitors of HIF-α may be administered at a concentration effective to prevent or reduce one or more symptoms of GvHD in a subject that has received transplanted allogeneic stem cells as compared to a control subject receiving transplanted allogeneic stem cells without one or more HIF-α inhibitors. For prevention, the drug should be injected before the onset of GVHD, for example between two weeks before to two months after HSC transplantation, preferably between a week before to one month after HSC transplantation. For treatment, the drug should be dosed as soon as possible after the diagnosis of GVHD or any time after the onset of GVHD. The frequency can be twice daily, daily, once every 2-7 days or even monthly depending on the formulation of Echinomycin, at doses and duration tolerated by the GVHD patients or till GVHD is effectively controlled.

In some embodiments, the one or more inhibitors of HIF-α are administered to a subject in combination with another GvHD treatments, such as the administration of a calcineurin inhibitor (e.g. cyclosporine or tacrolimus) with methotrexate. In some embodiments, tacrolimus administration begins on day −3 of HSC transplantation by Intravenous or oral dosing. For intravenous dosing the recommended starting dose is 0.03 mg/kg/day based on adjusted body weight as a continuous infusion. For oral dosing the recommended starting dose is 0.045 mg/kg/dose twice daily. Patients who cannot tolerate tacrolimus, then cyclosporine at a dose of 100× the intravenous tacrolimus dose (e.g., 3 mg/kg/day starting dose) is recommended. For oral dosing the recommended conversion is 3× the intravenous dose. When Neoral brand is used, because of greater bioavailability, the conversion is 2× the IV dose.

In some embodiments, methotrexate is used in combination with tacrolimus for GvHD prophylaxis. In some embodiments, methotrexate is given intravenously at a dose of 15 mg/m$^2$/dose once daily on Day 1 after HSC transplantation, and at a dose of 10 mg/m$^2$/dose on days 3, 6, and 11 after HSC transplantation.

Other treatments for GVHD include non-selective or selective inhibition or depletion of T cells to limit expansion of alloreactive T cells that mediate tissue injury. Non-selective T-cell depleting strategies include, but are not limited to, administration of antithymocyte globulin. Selective T-cell depleting/inhibition strategies include, but are not limited to, targeting one or more pro-inflammatory cytokines such as TNFα, IL-1, 11-6, IL-10 and chemokines.

In some embodiments, the one or more inhibitors of HIF-α are administered to a subject in combination with an effective amount of one or more immunosuppressive agents. In some embodiments, the one or more immunosuppressive agents comprise an agent that enhance regulatory T cell (Treg) activity. Examples of agents that enhance regulatory T cell (Treg) activity include, but are not limited to, rapamycin, Ihydroartemisinin, anti-IL2 monoclonal antibody that enhance IL-2 function in vivo, IL-2, anti-TNFs agents, JAK inhibitors (e.g. Tofacitinib), anti-IL17/IL17R agents (e.g. Brodalumab), antibodies targeting the a chain (CD25) of the IL-2 receptor (Basiliximab/Simulect; Daclizumab/Zinbryta), and anti-CD3 agents.

Symptoms of GvHD include sclerotic skin, limitation of oral intake, dryness of eyes, gastrointestinal (GI) tract symptoms such as dysphagia, anorexia, nausea, vomiting, abdominal pain, or diarrhea, liver symptoms as manifested by elevated bilirubin, elevated alkaline phosphatase, elevated alanine aminotranferease (ALT)/aspartate aminotransferase (AST) (AST/ALT) ratio, shortness of breath, and/or tightness of arms or legs. A subject may exhibit multiple symptoms depending on the tissue that is affected by GvHD. Some patients may exhibit 4-5 symptoms, while others may exhibit 1-2 symptoms.

The appropriate dosage ("therapeutically effective amount") of the HIF-α inhibitor will depend, for example, on the condition to be treated, the severity and course of the condition, the mode of administration, whether the inhibitor is administered for preventive or therapeutic purposes, the bioavailability of the inhibitor(s), previous therapy, the age and weight of the patient, the patient's clinical history and response to the antibody, the type of HIF-α inhibitor used and its $IC_{50}$ and/or $EC_{50}$ concentrations, discretion of the attending physician, etc. As used herein, the term "$IC_{50}$ concentration" refers to the inhibitor concentration that is required for 50% inhibition in vitro. The term "$EC_{50}$ concentration" refers to the inhibitor concentration in plasma that is required for 50% inhibition in vivo.

HIF-α inhibitor dosages can be tested in a suitable immunodeficient animal model as further described below. As a general proposition, the therapeutically effective amount of the HIF-α inhibitor will be in the range of about 1 ng/kg body weight/day to about 10 mg/kg body weight/day whether by one or more administrations. In particular embodiments, each HIF-α inhibitor is administered in the range of from about 1 ng/kg body weight/day to about 1 mg/kg body weight/day, about 1 ng/kg body weight/day to about 0.1 mg/kg body weight/day, about 1 ng/kg body weight/day to about 10 µg/kg body weight/day, about 1 ng/kg body weight/day to about 1 µg/kg body weight/day, about 1 ng/kg body weight/day to about 0.1 µg/kg body weight/day, about 1 ng/kg body weight/day to about 10 ng/kg body weight/day, about 10 ng/kg body weight/day to about 10 mg/kg body weight/day, about 10 ng/kg body weight/day to about 1 mg/kg body weight/day, about 10 ng/kg body weight/day to about 0.1 mg/kg body weight/day, about 10 ng/kg body weight/day to about 10 µg/kg body weight/day, about 10 ng/kg body weight/day to about 1 µg/kg body weight/day, about 10 ng/kg body weight/day to about 0.1 µg/kg body weight/day, about 100 ng/kg body weight/day to about 10 mg/kg body weight/day, about 100 ng/kg body weight/day to about 1 mg/kg body weight/day, about 100 ng/kg body weight/day to about 0.1 mg/kg body weight/day, about 100 ng/kg body weight/day to about 10 µg/kg body weight/day, about 100 ng/kg body weight/day to about 1 µg/kg body weight/day, about 1 µg/kg body weight/day to about 10 mg/kg body weight/day, about 1 µg/kg body weight/day to about 1 mg/kg body weight/day, about 1 µg/kg body weight/day to about 0.1 mg/kg body weight/day, about 1 µg/kg body weight/day to about 10 µg/kg body weight/day, about 10 µg/kg body weight/day to about 10 mg/kg body weight/day, about 10 µg/kg body weight/day to about 1 mg/kg body weight/day, about 10 μg/kg body weight/day to about 0.1 mg/kg body weight/day, about 100 μg/kg body weight/day to about 10 mg/kg body weight/day, about 100 μg/kg body weight/day to about 1 mg/kg body weight/day, about 1 mg/kg body weight/day to about 10 mg/kg body weight/day.

In other embodiments, each HIF-α inhibitor is administered in the range of about 10 ng to about 100 ng per individual administration, about 10 ng to about 1 μg per individual administration, about 10 ng to about 10 μg per individual administration, about 10 ng to about 100 μg per individual administration, about 10 ng to about 1 mg per individual administration, about 10 ng to about 10 mg per individual administration, about 10 ng to about 100 mg per individual administration, about 10 ng to about 1000 mg per injection, about 100 ng to about 1 μg per individual administration, about 100 ng to about 10 μg per individual administration, about 100 ng to about 100 μg per individual administration, about 100 ng to about 1 mg per individual administration, about 100 ng to about 10 mg per individual administration, about 100 ng to about 100 mg per individual administration, about 100 ng to about 1000 mg per injection, about 1 μg to about 10 μg per individual administration, about 1 μg to about 100 μg per individual administration, about 1 μg to about 1 mg per individual administration, about 1 μg to about 10 mg per individual administration, about 1 μg to about 100 mg per individual administration, about 1 μg to about 1000 mg per injection, about 10 μg to about 100 μg per individual administration, about 10 μg to about 1 mg per individual administration, about 10 μg to about 10 mg per individual administration, about 10 μg to about 100 mg per individual administration, about 10 μg to about 1000 mg per injection, about 100 μg to about 1 mg per individual administration, about 100 μg to about 10 mg per individual administration, about 100 μg to about 100 mg per individual administration, about 100 μg to about 1000 mg per injection, about 1 mg to about 10 mg per individual administration, about 1 mg to about 100 mg per individual administration, about 1 mg to about 1000 mg per injection, about 10 mg to about 100 mg per individual administration, about 10 mg to about 1000 mg per injection, about 100 mg to about 1000 mg per injection. The HIF-α inhibitor may be administered twice a day, daily, or every 2, 3, 4, 5, 6 or 7 days, or every 1, 2, 3 or 4 weeks.

In one embodiment, the HIF-α inhibitor is administered to a human subject at a dose of 0.1 mg to 1000 mg every day or every other day for a period needed to cure GVHD or maximally tolerable by the GVHD patients. In other particular embodiments, the amount of the HIF-α inhibitor is administered to a human subject at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage will be dependent on the condition, size, age and condition of the patient.

Where the HIF-α inhibitor is echinomycin, the dose range is at least about 1 μg/kg, usually at least about 10 μg/kg, at least about 50 μg/kg, and not more than about 10 mg/kg, usually not more than about 1 mg/kg. Where the HIF-α inhibitor is not echinomycin, the inhibitor may be administered at a concentration providing an equivalent amount of HIF-α inhibitory activity.

Monitoring HIF-1α and/or HIF-2α Expression

In some embodiments, the method further comprises the step of monitoring the expression of HIF-1α and/or HIF-2α in the subject. The expression level of HIF-1α and/or HIF-2a could provide a useful marker for determining whether to administer the HIF-α inhibitor, as well as the dose and frequency of administration. In some embodiments, the expression of HIF-1α in the CD4$^+$ and/or CD8$^+$ T cell of the subject is monitored. In some embodiments, the expression of HIF-1α in the CD4$^+$ and/or CD8$^+$ T cells in the bone marrow of the subject is monitored. In some embodiments, the expression of HIF-1α in the CD4$^+$ and/or CD8$^+$ T cells in the peripheral blood of the subject is monitored. Methods for determining or measuring HIF-1α and/or HIF-2α expression on T cells are well known in the art. In some embodiments, the method of preventing GvHD or the method of treating GvHD includes the step of monitoring the expression of HIF-1α and/or HIF-2α on the CD4$^+$ and/or CD8$^+$ T cell of the subject. In some embodiments, the treatment regimen, such as the dose and duration of treatment may be adjusted based on the expression level of HIF-1α and/or HIF-2α on the CD4$^+$ and/or CD8$^+$ T cell of the subject.

Humanized GvHD Animal Model

Another aspect relates to a humanized GvHD animal model and a method for generating the humanized GvHD animal model. In one embodiment, a method for generating a humanized GvHD animal model comprises conditioning an immunodeficient mouse by whole body irradiation or drug-induced myeloid ablation, and engrafting the conditioned mouse with a sufficient number of human bone marrow cells to cause GvHD. Another embodiment relates to a humanized GvHD mouse model generated in accordance with these method steps.

As used herein, the term "immunodeficient" refers to an animal's impaired or otherwise not fully functioning immune system, for example an inability to produce a normal amount of B-cells, T-cells, NK-cells, etc. Immunodeficiency may be produced by, for example, but not limited to, mutations, irradiation, a chemical or pharmaceutical, or a virus. Examples of immunodeficient mice include but are not limited to NSG mice (NOD/SCID/γc$^{-/-}$; or NOD/scid IL2rγ$^{null}$), NOG mice (NOD/γc$^{-/-}$ or NOD/scid/IL2rγ$^{Trunc}$), NOD mice (non-obese diabetic), SCID mice (severe combined immunodeficient mice), NOD/SCID mice, nude mice, BRG mice (BALB/c-Rag2$^{null}$/IL2rγ$^{null}$), Rag 1$^{-/-}$ mice, Rag 1$^{-/-}$/γc$^{-/-}$ mice, Rag 2$^{-/-}$ mice, and Rag 2$^{-/-}$/γc$^{-/-}$ mice.

In some examples, mice that have been cross-bred with any of the above-referenced mice and have an immunocompromised background may be used for implanting HSCs as described herein. In some examples, the immune deficiency may be the result of a genetic defect in recombination, a genetically defective thymus, a defective T-cell receptor region, a NK cell defect, a Toll receptor defect, an Fc receptor defect, an immunoglobulin rearrangement defect, a defect in metabolism or any combination thereof. In some examples, mice are rendered immunodeficient by administration of an immunosuppressant, e.g., cyclosporin, NK-506, removal of the thymus, or radiation.

Exemplary immunodeficient mouse strains for use in the present methods include, but are not limited to, NOD.Cg-Prkdc$^{scid}$Il2rg$^{tm1Wjl}$ (NSG), NOD.Cg-PRdc$^{scid}$IL2rg$^{tm1Sug}$ (NOG), and C.Cg-Rag2$^{tm1Fwa}$ Il2rg$^{tm1Sug}$ (BRG). Immunodeficient mouse strains are available from The Jackson Laboratory (http://www.jax.org/) and Taconic Biosciences, Inc. (www.taconic.com).

Following the completion of the conditioning steps in accordance with the above description, the mammalian subject is transplanted with a suitable amount of bone marrow cells (as further described above), thereby resulting in GvHD. In a particular embodiment, bone marrow comprising between 0.01-10×10⁶ mononuclear cells is engrafted into a conditioned mouse. The cells may be injected into a recipient immunodeficient mouse intra-hepatically, intraperitoneally, or subcutaneously.

The use of bone marrow cells as the source of engrafted cells, allows for the reproducible production of a GvHD model system faithfully recapitulating the pathological features of human GvHD as further described in the EXAMPLES below.

A further aspect of the present application relates to a method of identifying drug candidates for treatment of GvHD, comprising the steps of: administering a test agent into an immunodeficient mouse with humanized systemic GvHD generated using the method of the present application, monitoring survival and clinical manifestations of GvHD in the mice, and identifying the test agent as a candidate drug for GvHD if the test agent prevents or reduces the severity GvHD in the mouse compared to a mouse with humanized systemic GvHD receiving a control agent. In some embodiments, the mouse with humanized systemic GvHD is generated by transplanting human bone marrow cells into a newborn NSG mouse.

EXAMPLES

Example 1: Materials and Methods

1. Mice.

All procedures involving experimental animals were approved by the Institutional Animal Care and Use Committees of the Children's Research Institute where this work was performed. Nod.Scid.Il2rg0(NSG) mice were purchased from the Jackson Laboratory and were bred and maintained under specified pathogen-free conditions in research animal facilities at the Children's Research Institute.

2. Xenografting of Human BM Cells into Newborn NSG Pups.

Human bone marrow mononuclear cells were isolated from healthy human adult bone marrow using density gradient separation were purchased from Stemcell Technologies (Vancouver, Canada) and Lonza (Walkersville, Md., USA). Human CD3⁺ cells from BM were sorted from human BM cells using BD Influx (BD Biosciences). Cells were thawed, counted and re-suspended in 1×PBS in a concentration of 0.1-0.5×10⁶ per 30 μl. 0.1-0.5×10⁶ cells were transplanted via intrahepatic injection into irradiated (1.30 Gy) newborn NSG pups. Human CD45⁺ cells in PBMC of recipients were detected by FACS analysis at day 17 to 20 after transplantation.

3. Flow Cytometry.

Peripheral blood was collected by sub-mandibular bleeding at different times after transplantation of human BM cells. Fluorochrome-labeled antibodies were directly added into whole blood. After 30 min of staining, the unbound antibodies were washed away and the red blood cells were lysed with BD FACS™. The stained cells were analyzed with BD FACS Canto II flow cytometry.

Spleens were gently grinded with frosted objective slides and bone marrow was dissociated with syringes to obtain single-cell suspensions and passed through a nylon cell strainer, washed three times with RPMI-1640, labeled with antibodies and analyzed for the presence of different human cell populations.

Antibodies used were phycoerythrin (PE) conjugated anti-human CD45, anti-human FoxP3, PE-Cy7 conjugated anti-human CD4, allophycocyanin (APC) conjugated anti-human CD11c, anti-human FoxP3, anti-mouse CD45, eFluor 450 conjugated anti-human CD3, eFluor 780 conjugated anti-human CD19 (eBioscience, San Diego, Calif.), peridinin chlorophyll protein conjugated (PerCP) anti-human CD14, fluoresceinisothiocyanate (FITC) conjugated anti-human CD8, V500 conjugated anti-human CD14 (BD Bioscience, San Jose, Calif.), and PE-Cy 7 conjugated anti-human CD11b (BioLegend). PE, PerCP and APC conjugated anti-human HIF-1α were obtained from RD Systems (Minneapolis, Minn.).

4. Immunofluorescence.

Immunohistochemistry was performed on tissue sections from skin, liver, lung, spleen, and kidney of humanized NSG mice. Sections were fixed with 4% paraformaldehyde and dehydrated with graded alcohol. After treatment with heated citrate buffer for antigen retrieval, sections were blocked for endogenous peroxidase activity. Sections were then incubated in 10% goat serum followed by primary antibodies at 4° C. overnight. Fixed samples were stained with the following antibodies, anti-human CD45 (MEM-28) and CD3 (ab828, Abcam PLC, Cambridge, Mass.), for detection of infiltrated human cells. After incubation for 30 minutes with secondary antibody, the specimens were visualized by DAB treatment. Sections were lightly counterstained with hematoxylin to enable visualization of nuclei.

5. Pathology Scores.

The organs of moribund mice were fixed in formalin and sectioned for hemoxylin and eosin (H&E) staining. All sections were scored based on the following criteria. Grade 0, no lesions; grade 1, minimal perivascular leukocyte infiltrations; Grade 2, Mild perivascular leukocyte infiltrations; Grade 3, moderate perivascular leukocyte infiltrations, with leukocyte infiltration into parenchyma, tissue cell necrosis; Grade 4, Moderate to severe perivascular leukocyte infiltration, with intra-parenchymal leukocytes and tissue cell necrosis.

6. Treatment of GvHD Mice with Echinomycin.

Newborn NSG pups received 0.3-0.5×10⁶ human BM cells intrahepatically. Beginning on day 17 or 27, the recipients received 5 intraperitoneal injections of echinomycin, daily at 10 μg/kg. Following 2 days of rest, another 5 intraperitoneal injections of echinomycin were administered at the same dose, once per day. The second round of treatment was performed following 5 days of rest from the prior round of treatment, using the same dose once every other day for 10 total treatments.

Example 2: Transplantation of Human BM Cells Into Newborn NSG Pups Causes GvHD To develop a robust mouse model for human GvHD, 0.5×10⁶ human BM cells were transplanted into newborn NSG mice and followed the engraftment and expansion of human leukocytes, as well as survival of the chimera mice. Exemplary data for one of the recipients is presented in FIG. 1.

As illustrated in FIG. 1, Panel A and summarized in FIG. 1, Panel B, robust engraftment and expansion of human leukocytes were observed in the blood of the recipient mice on day 17, as an average of 40% human leukocytes were observed in the PBL. Among them, the overwhelming majority expressed T cell markers CD4 and/or CD8. As reported by others, approximately 10% of human T cells express both CD4⁺ and CD8⁺, although the function of this subset is unclear. Longitudinal studies showed gradual expansion of human cells until they surpassed mouse leukocytes (FIG. 1, Panel C). The first sign of GvHD is observable within two weeks, as judged by retarded growth (FIG. 1, Panel D) and damage to the skin and lack of hair growth (data not shown). Morbidity and/or mortality were observed starting on the third week, and essentially all mice die within six weeks (FIG. 1, Panel E). Similar engraftment and mortality were observed with three additional donors (data not shown).

To test if human CD3$^+$ caused GvHD in the recipient mice, human BM cells were sorted into CD3$^+$ and CD3$^-$ populations, followed by transplantation of equivalent numbers of either CD3$^+$, CD3$^-$, or unsorted bone marrow cells (BMC) into the recipient mice. As shown in FIG. 1, Panel F, recipients of CD3$^+$ cells, as well as unsorted BMC, developed severe GvHD and died within 30 days. Since the GvHD onset was faster in the recipients, T cells were likely responsible for GvHD. This is evidenced by the fact that recipients of CD3$^-$ cells did not develop GvHD during the observation period of 246 days (FIG. 1, Panel F). Thus, transplantation of a very low number of human BM cells into newborn NSG pups causes severe xenogeneic GvHD, and CD3$^+$ cells contribute to the GvHD in this humanized mouse model.

Example 3: Infiltration of Human T Cells Into Peripheral Tissues

Figure 2B:
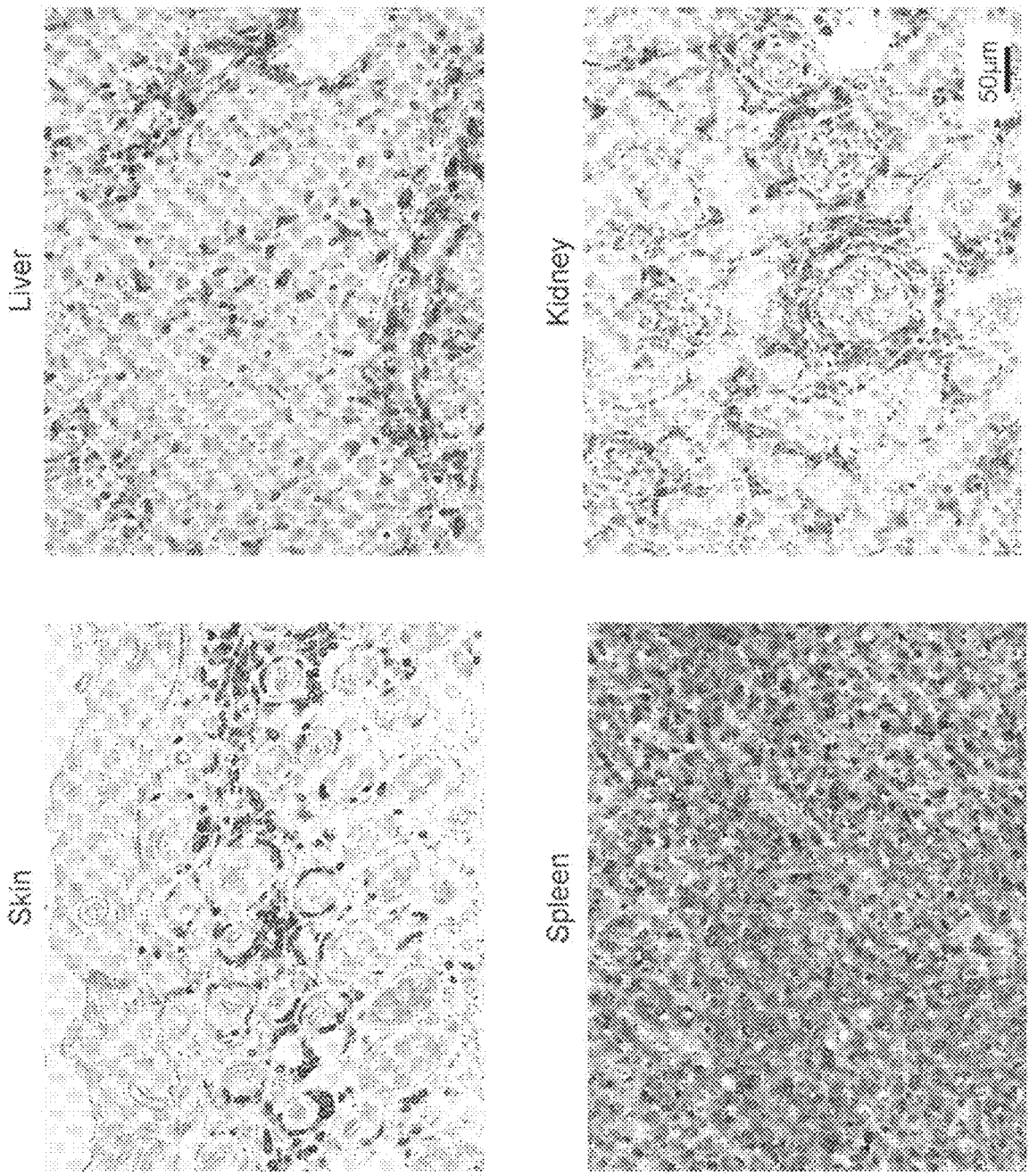
FIG. 2. Histopathology and immunohistochemistry analyses for infiltration of human $CD3^+$ cells in the organs of xenogeneic NSG recipients. Panel A. Representative hematoxylin and eosin (H&E) staining of tissue sections obtained from skin, liver, kidney, tongue, lung, pancreas, stomach and intestine of GvHD mice. Panel B. Representative immunohistochemical staining with anti-human CD3 shows that a high proportion of $CD3^+$ cells had infiltrated various organs of human BM NSG recipients. This immunohistochemical evaluation was performed in 20 mice. Tissues were formalin fixed and paraffin embedded.
Figure 3A:
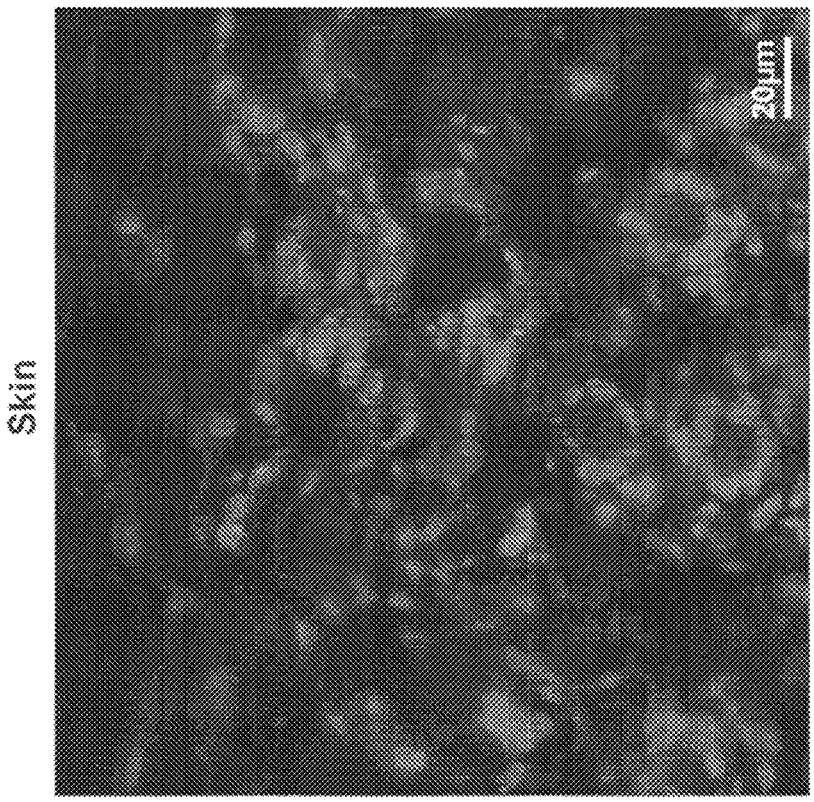
FIG. 3. Distribution of human cells in the organs of xenogeneic NSG recipients as revealed by immunofluorescence. Panel A. Distribution of human $CD4^+$ and $CD8^+$ cells in the organs of xenogeneic NSG recipients. Immunofluorescence staining with anti-human CD4 and CD8 shows the distribution of $CD4^+$ and $CD8^+$ T cells in various organs of human BM NSG recipients. This immunofluorescence evaluation was performed in 15 mice. Panel B. Distribution of human $CD3^+$ and $CD45^+$ cells in the organs of xenogeneic NSG recipients. Immunofluorescence staining with anti-human CD3 and CD45 shows the distribution of $CD3^+$ and human $CD45^+$ cells in various organs of xenogeneic NSG recipients. This immunofluorescence evaluation was performed in 15 mice. Tissues were formalin fixed and paraffin embedded. Data are representative of three independent experiments.
Figure 3A:
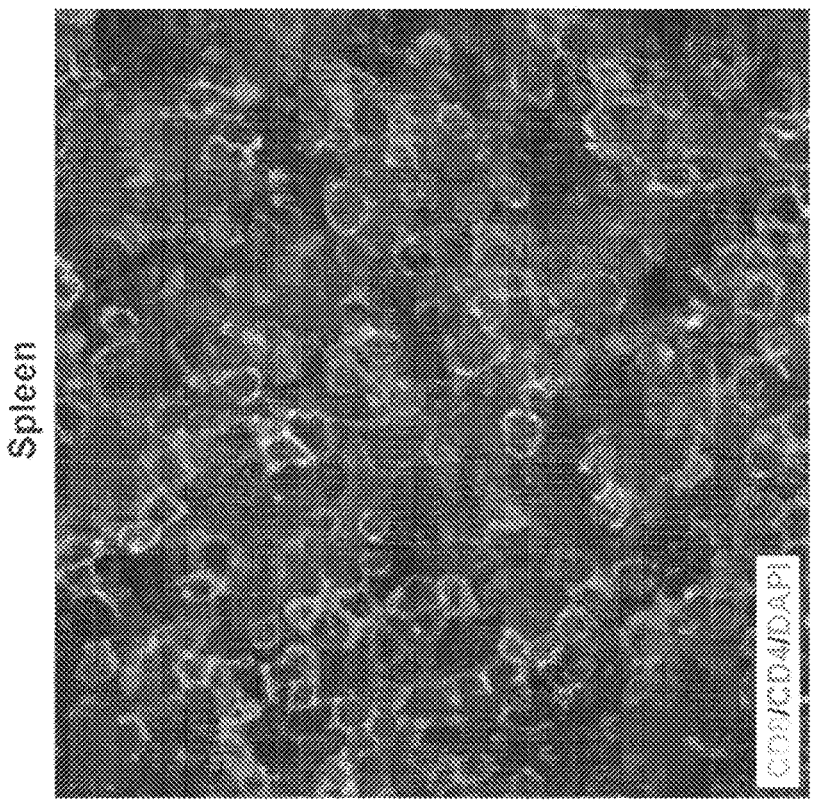
Figure 3B:
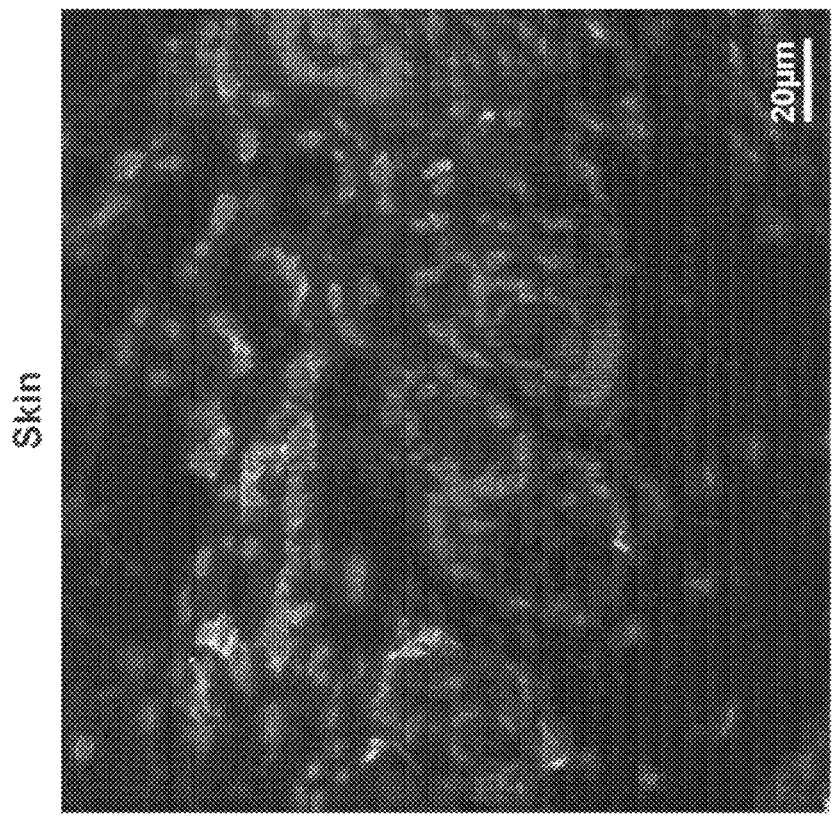
Figure 3B:
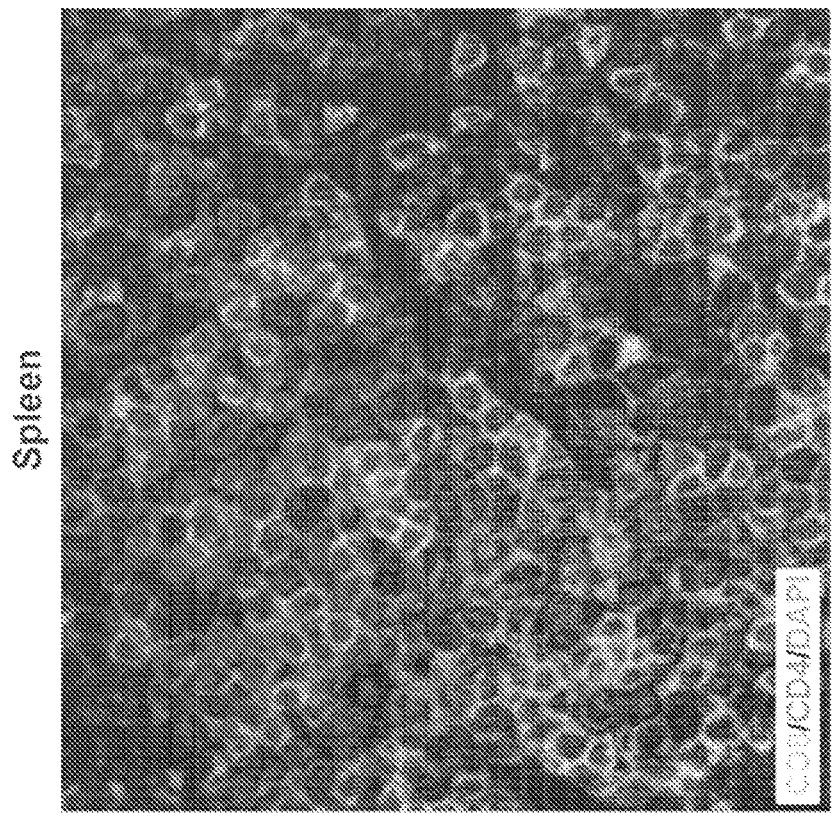

Based on H&E staining, the BMT recipients exhibited extensive inflammation in multiple organs (FIG. 2, Panel A, and Table 1). Immunohistochemical examination of the spleen, skin, liver, kidney, lung, pancreas, stomach and intestine of mice developing clinical symptoms of xenogeneic GvHD revealed the detection of human CD3$^+$ T cells in these tissues (FIG. 2, Panel B). Infiltration by human T cells was highest in the spleen and lungs, although a high degree of infiltration was also apparent in the other tissues. In the lung, there were multifocal aggregates of human cells that expanded into the alveolar septa. In addition, a dramatic thickening of the skin, accompanied by human T cell infiltration along the dermal-epidermal junction was observed. Table 1 shows infiltration scores reflecting human T cell infiltration in different tissues with a score of 4 representing the highest degree of infiltration with moderate to severe perivascular leukocyte infiltration, intra-parenchymal leukocytes and tissue cell necrosis. A high level of infiltration was observed in all of the tissues examined.

TABLE 1

Summary of infiltration scores in organs of xenogeneic GvHD mice.

|  | Lung | Liver | intenstine | skin | kidney | stomach |
| --- | --- | --- | --- | --- | --- | --- |
| no human BM (n = 3) | 0 | 0 | 0 | 0 | 0 | 0 |
| BM (Donor 1) (n = 3) | 3.3 ± 0.7 | 2.7 ± 0.3 | 2.7 ± 0.3 | 2.7 ± 0.3 | 2.5 ± 0.5 | 2.5 ± 0.5 |
| BM (Donor 2) (n = 5) | 3.6 ± 0.4 | 3.3 ± 0.6 | 3.3 ± 0.6 | 3.0 ± 0 | 3.3 ± 0.6 | 3.3 ± 0.6 |
| BM (Donor 3) (n = 7) | 3.7 ± 0.6 | 3.7 ± 0.6 | 3.7 ± 0.6 | 3.7 ± 0.6 | 3.7 ± 0.6 | 3.7 ± 0.6 |
| BM (Donor 4) (n = 5) | 3.8 ± 0.2 | 3.6 ± 0.4 | 3.6 ± 0.4 | 3.8 ± 0.2 | 3.8 ± 0.2 | 3.8 ± 0.2 |

To further examine the distribution pattern of the T cells, localization of human CD4$^+$ and CD8$^+$ T cell subsets in the various organs of xenogeneic GvHD mice was investigated using immunofluorescence staining. As shown in FIG. 3, Panel A, CD8$^+$ T cells account for over 80% of the human lymphocytes in organs such as the liver, lung, skin, kidney, and intestine. This data demonstrates that CD4$^+$ and CD8$^+$ T cell subsets each contribute to the phenotype, and that CD8$^+$ T cells may play a dominant role. To test for infiltration of other human cell types into the organs, immunofluorescence staining with anti-human CD3 and CD45 antibodies was performed (FIG. 3, Panel B). Virtually 100% of human cells (CD45$^+$) that had infiltrated the organs were T cells (CD3$^+$); very few CD45$^+$CD3$^-$ cells were found in the tissues. Together, this data suggests that T cells are responsible for these observed phenotypes in this BMT-GvHD model.

Figure 4:
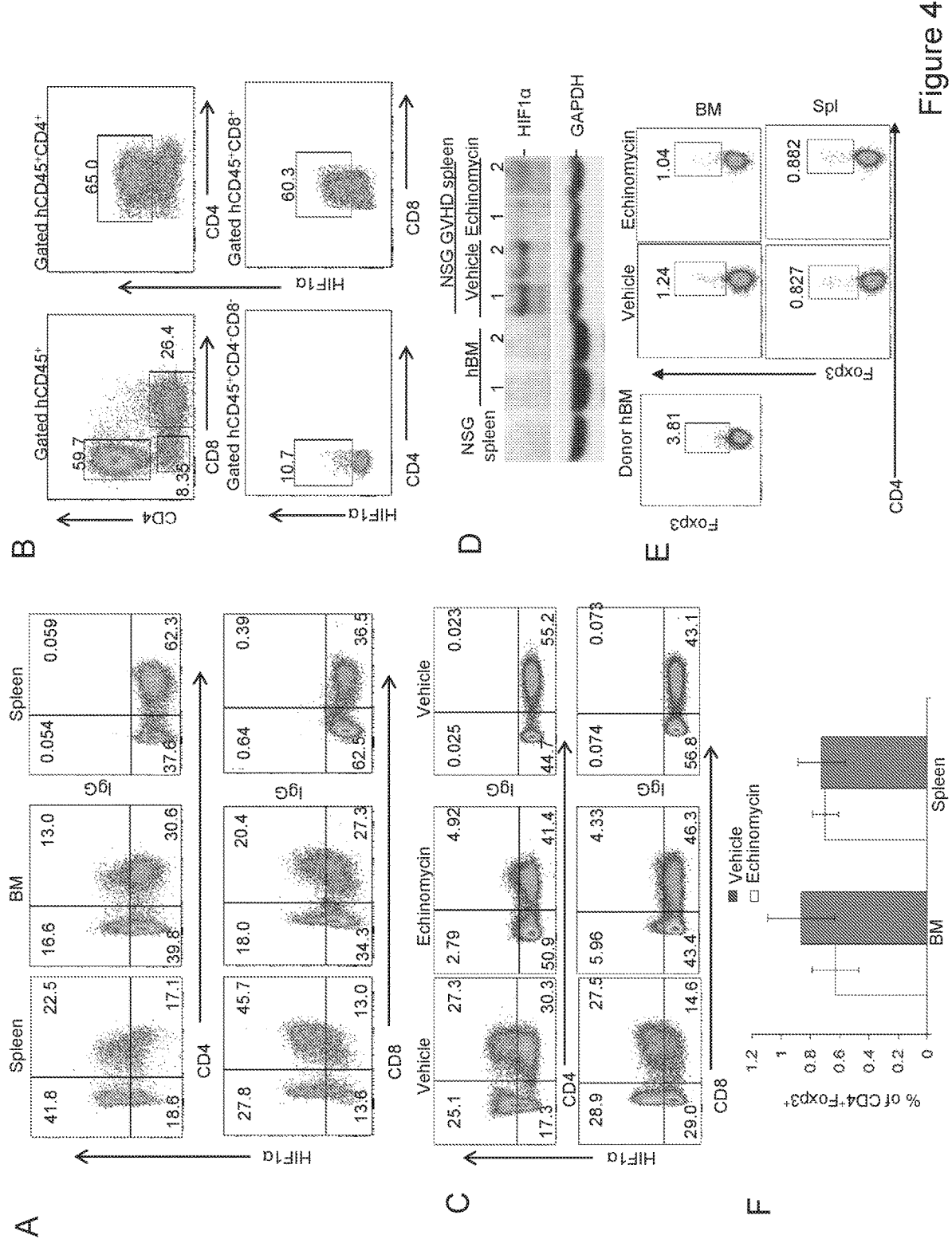
FIG. 4. HIF-1α accumulates in a high proportion of human T cells derived from spleen and BM of the recipients of human BMC: Impact of echinomycin. Panel A. Representative FACS plots showing the accumulation of HIF-1α in T cells from the spleen and BM of GvHD mice. Spleen and BM cells were isolated from the spleens and BM of GvHD mice, stained with anti-human CD45, CD4, CD8, and then intracellular stained with anti-human HIF-1α. Panel B. Representative FACS plots showing the accumulation of HIF-1α in all human cells from spleens of GvHD mice. Spleen cells were isolated from the spleens of GvHD mice, stained with anti-human CD45, CD4, CD8, and then intracellular stained with anti-human HIF-1α. FACS analysis was performed to determine the percentage of HIF-1α positive cells in $CD45^+CD4^+CD8-$, $CD45^+CD4-D8^+$ and $CD45^+CD4-D8$-subpopulations. Panel C. Representative FACS plots showing the percentage of HIF-1α positive T cells in spleen of GvHD mice after echinomycin treatment. Spleen cells were isolated from spleen of GvHD mice treated with one dose of 100 μg/kg of echinomycin or vehicle, stained with anti-human CD45, CD4, CD8, and then intracellular stained with anti-human HIF-1α. Data are representative of three independent experiments. Panel D. Western blot analysis of HIF-1α in spleen cells from GvHD recipients after echinomycin treatment. Spleen cells from GvHD mice were isolated and protein lysates were subjected to immunoblot with anti-human HIF-1α. Protein levels of HIF-1α in human BM (hBM) and spleen cells from two vehicle- and echinomycin-treated GvHD mice were examined by Western blot. GAPDH served as a loading control. Data is one representative image from 3 mice and representative of three independent experiments. Panel E and Panel F. Echinomycin treatment does not expand human Treg in the NSG recipients of hBM. Spleen and BM cells were isolated from spleen and hind femur of GvHD mice treated with one dose of 100 μg/kg of echinomycin or vehicle, stained with anti-human CD45, CD4, CD8, and then intracellular stained with anti-human FoxP3. Data are representative of three independent experiments. Representative FACS profiles are shown in Panel E, while summary data (Means and SEM) are shown in Panel F.

Example 4: Accumulation of HIF-1α is Critical for the Maintenance of Activated T Cells in GvHD Mice HIF-1α plays a critical role in driving T cell differentiation, metabolism and cytotoxic activity (Palazon, A. et al., *Immunity*, 41(4):518-528 (2014)). However, the role of HIF-1α in GvHD has not been previously investigated. Detection of HIF-1α expression was therefore investigated by intracellular staining of cells isolated from the spleen and BM of GvHD recipients. To examine which T cell subsets were accumulating high levels of HIF-1α, isolated BM and spleen cells were stained with anti-human CD45, CD4, CD8 and HIF-1α and subjected to FACS analysis. HIF-1α was detectable at high levels in CD4$^+$ and CD8$^+$ T cell subsets (FIG. 4, Panel A). Surprisingly, while approximately 40% of CD8 T cells in BM from the recipient mice are HIF-1α$^+$, more than 70% of CD8 T cells in the spleen express HIF-1α (FIG. 2, Panel A). Since the spleen is normally well oxygenated, HIF-1α protein must be resistant to oxygen-mediated degradation. This accumulation under normoxic conditions is similar to what was reported in leukemia stem cells (Wang, Y. et al., *Cell Stem Cell*, 8(4):399-411 (2011)). In contrast, only 10% of CD4$^-$CD8$^-$ cells in the spleen express HIF-1α (FIG. 2, Panel B).

To test the significance of HIF-1α accumulation, GvHD recipient mice were treated with echinomycin, a selective inhibitor of HIF-1α. Surprisingly, the HIF-1α$^+$ cells lost HIF-1α protein overnight following a single dose of echinomycin treatment (FIG. 4, Panel C). Since the T cell frequencies were largely unaffected, echinomycin must have reduced expression of HIF-1α rather than eliminated the HIF-1α-expressing cells. Further, spleen cells from GvHD mice were isolated and human HIF-1α protein levels from echinomycin-treated mice and vehicle controls were measured by western blot analysis. HIF-1α protein levels were significantly decreased in the spleen cells of echinomycin-treated mice as compared to those of vehicle controls. Since HIF-1α was absent in the human BM cells used for the GvHD induction and in NSG recipient that received no BMT (FIG. 4, Panel D), accumulation of HIF-1α protein must have occurred following GvHD induction.

It has been reported that HIF-1α antagonizes FoxP3 by regulating and interacting with FoxP3 to regulate T cell activation[17,18]. To assess whether this xeno-GvHD model system was influenced by Treg cells via a FoxP3-HIF-1α mediated regulatory circuit, the effect of HIF-1α inhibition on the percentage of FoxP3+ cells within the CD4 T cell subset derived from the spleen and BM of either echinomycin treated or vehicle control mice was examined. There was no apparent difference in proportion of Tregs between echinomycin treated or vehicle control mice (FIG. 4. Panel E and Panel F). These results suggest that HIF-1α does not contribute much to maintenance of FoxP3+ human T cells in the NSG mice. However, since the frequency of the FoxP3+ T cells are much lower in the NSG mice than in the BM donor cells, it is possible that the NSG environment may not be suitable for expansion of human Treg cells.

Example 5: Echinomycin Treatment Protects Mice Against Lethal GvHD

Figure 5:
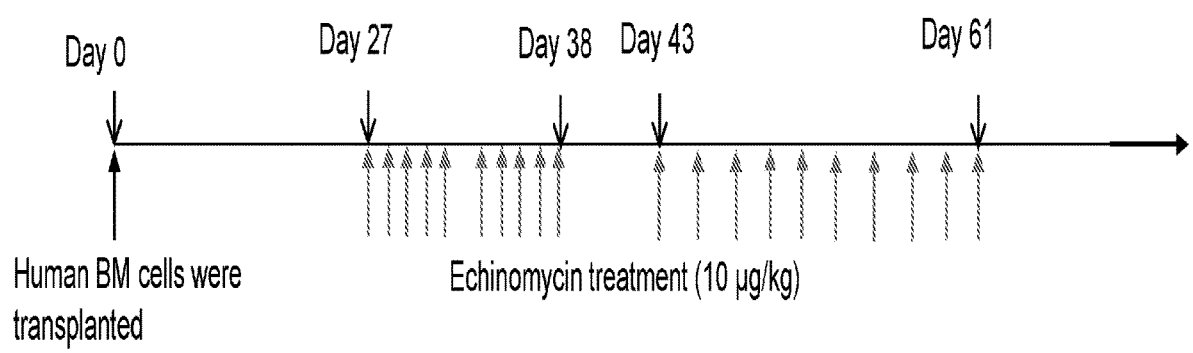
FIG. 5. Sustained treatment of echinomycin protects mice against GvHD and eliminates expanded human leukocytes and inflammation. Panel A. Dosing regimen of echinomycin treatment for humanized GvHD mice. The day that mice were transplanted with human BM cells is defined as day 0. Each arrow represents one echinomycin treatment. The dose for each treatment is 10 μg/kg via intraperitoneal injection. Panel B. Longitudinal analysis of clinical representation of an echinomycin-treated mice. Panel C. Representative FACS plots showing the percentage of human $CD45^+$ cells in PBL of GvHD mice before and after echinomycin treatment. Data is one representative file from 3 mice and representative of three independent experiments. Panel D. Immunohistochemical staining with anti-human CD3 shows a significant reduction of $CD3^+$ cells in the same mouse in FIG. 5, Panel B after echinomycin treatment at day 75 (bottom) and an untreated littermate, which died at day 55 after transplantation of human BM (Top). Data are representative of three independent experiments.
Figure 5:
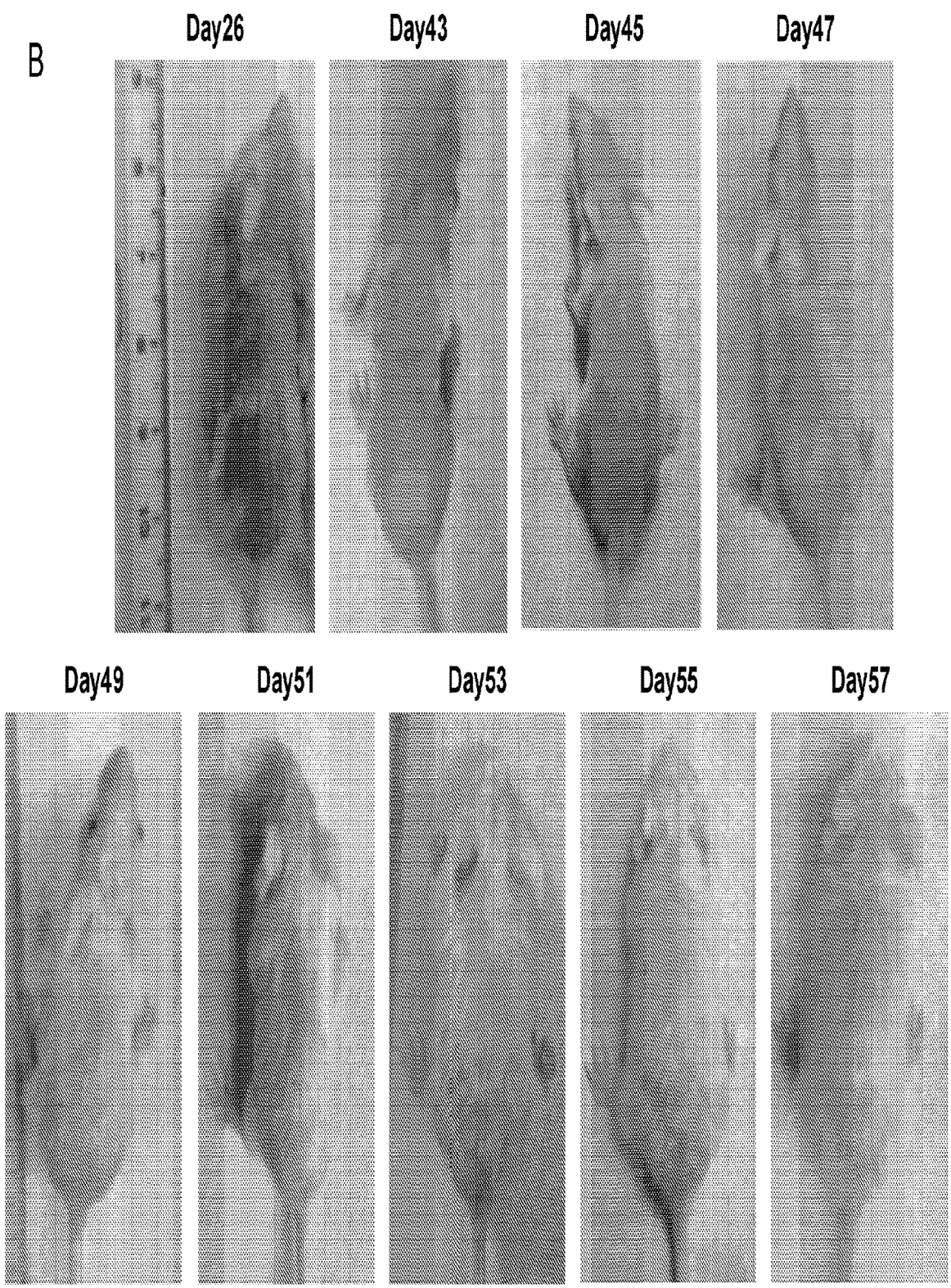
Figure 5:
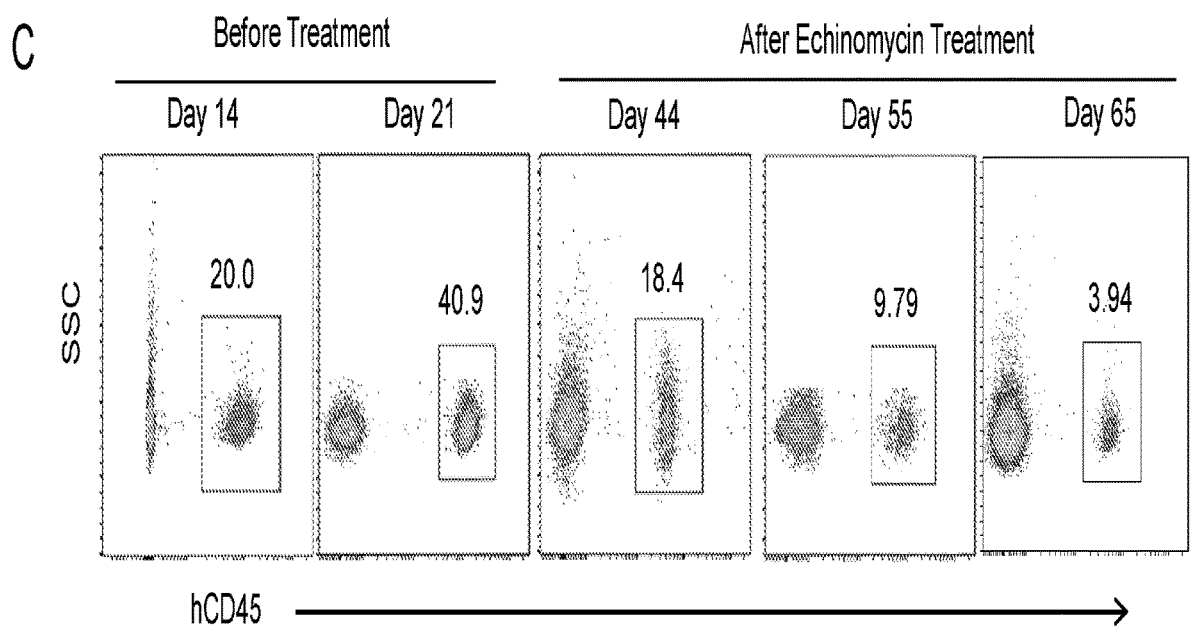
Figure 5D:
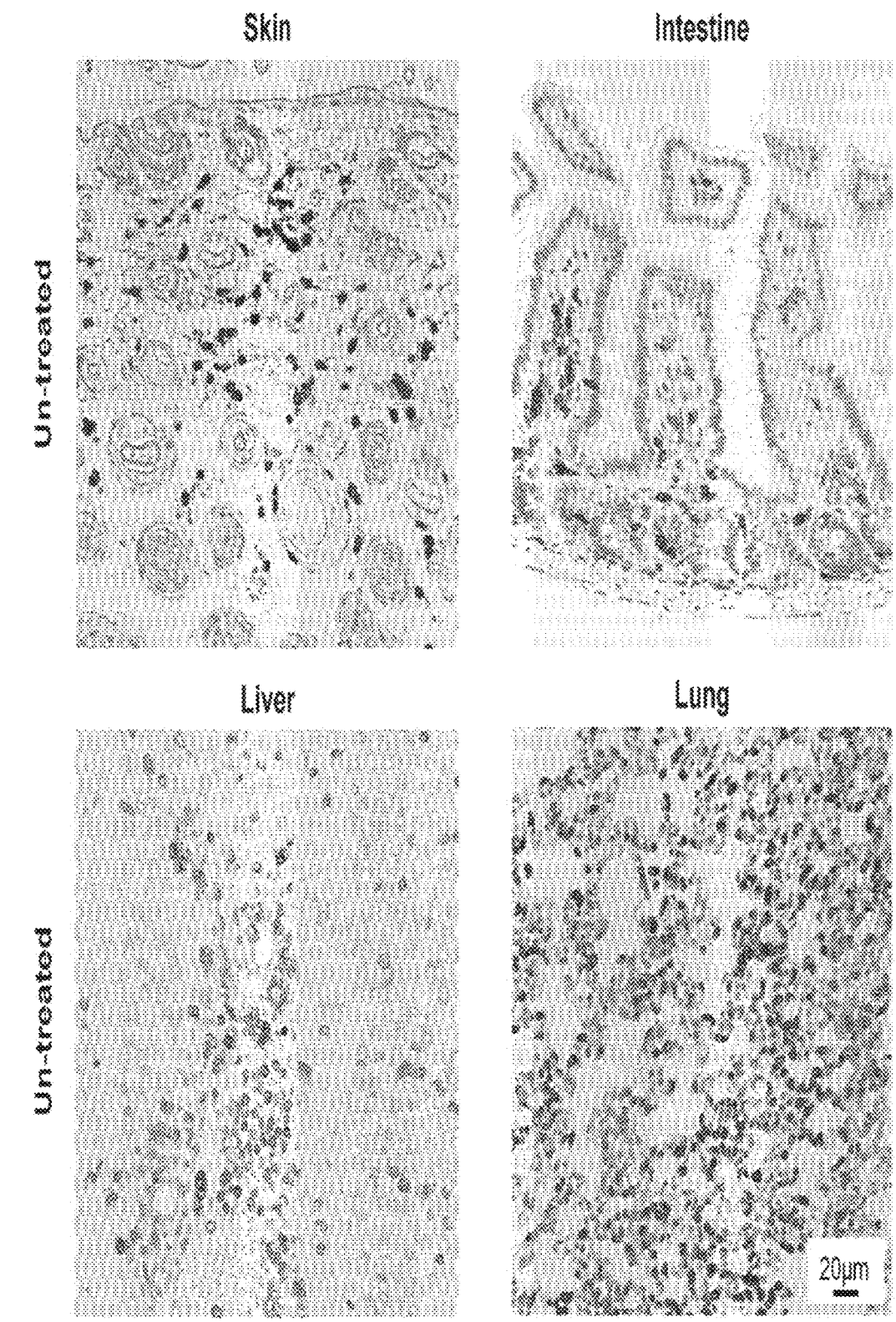

To better understand the importance of HIF-1α in the therapy of GvHD, the effect of HIF-1α inhibition was examined. Newborn pups were transplanted with 0.5×10⁶ human BM cells via intra-hepatic injection. Twenty-seven days after transplantation, mice were treated with 10 µg/kg of echinomycin for a total of 20 treatments. The therapeutic regimen is depicted in FIG. 5, Panel A and an example follow up of a treated mouse is shown in FIG. 5, Panel B. As shown in FIG. 5, Panel B, at day 26 after BMT, the mouse exhibited severe skin defects, including hairlessness, inflammation and thickened and dry skin. After two weeks of treatments, the mouse regained smooth skin with visible regrowth of hair. The mouse also showed normal growth over time, although the recovery of hair was incomplete. Corresponding to improvement in clinical symptoms, the number of human leukocytes in the peripheral blood was reduced by more than 10-fold over 5 weeks (FIG. 5, Panel C). IHC analyses revealed elimination of T cells from all major organs, including skin, intestine, liver and lung (FIG. 5, Panel D). Remarkably, while all of the vehicle treated mice died during the treatment period, echinomycin-treated mice survived.

With cessation of drug, the mice gradually succumb to GvHD. The median survival in the vehicle treated group is 51 days, while that of the echinomycin treated group is 99 days (FIG. 6, Panel A). Therefore, echinomycin extended the mouse life span even after cessation of treatment. To examine the therapeutic effect of echinomycin at the early stage of GvHD, 0.3×10⁶ BM cells were transplanted into newborn recipients, which were then treated at day 17 after transplantation. The median survival in the vehicle treated group is 50 days, while that of the echinomycin treated group is 119 days. The life span is 20 days longer than that of the mice treated with echinomycin starting at Day 27 (FIG. 6, Panel B). Data are representative of three independent experiments.

Compared with the currently used xenograft GvHD models caused by human PBL, the present animal model offers several advantages. First, while the PBL-induced GvHD causes damage by inflammation in the lung, this model recapitulates human pathology as severe inflammation was found in all clinically relevant organs, including the skin, gut, and liver. Second, the GvHD in this model is caused by T cells from human BM, which is the primary source of donor cells of HSCT in clinical practice. Third, the use of mouse pups rather than adults reduces the cost of animal care as most of the study can be completed prior to weaning.

Recent studies have shown that HIF-1α plays a critical role in driving T cell differentiation, metabolism and cytotoxic activity (Palazon, A. et al., *Immunity*, 41(4):518-528 (2014)). T cell activation both induces and stabilizes HIF-1α, leading to increased cytolytic activity of CD8+ T cells (Doedens, A. L. et al, *Nat Immunol.*, 14(11):1173-1182 (2013). The present results show that HIF-1α is greatly elevated during GvHD as the human T cells express high levels of HIF-1α, which can be eliminated by short-term treatment with echinomycin. Importantly, continuous treatment of echinomycin confers protection against lethal GvHD in nearly 100% of mice. The therapeutic effect is further confirmed in that essentially all mice died after cessation of drug. While the biological impact of HIF has been well documented in models of autoimmune diseases, cancer biology, cancer immunity and viral immunity (Peng, G. et al, *Trends Pharmacol. Sci.*, 36(6):374-83 (2015)), these results are the first to extend the role for HIF into the pathogenesis of GvHD.

GvHD is a major barrier to HSCT in leukemia patients. The data presented herein identifies HIF-1α as a therapeutic target and echinomycin and other HIFα inhibitors as potential therapeutics for the disease. Echinomycin (NSC526417) is a member of the quinoxaline family of antibiotics originally isolated from *Streptomyces echinatus* in 1957. Echinomycin is a DNA intercalating cyclic peptide that blocks the binding of HIF1α to HIF-responsive elements (HREs). Echinomycin was previously shown to be effective in treating experimental leukemia and lymphoma by targeting HIF-1α and eliminating leukemia stem cells without adverse reactions towards hematopoietic stem cells (Wang, Y. et al., *Cell Stem Cell*, 8(4):399-411 (2011); Wang, Y. et al., *Blood*, 124(7):1127-1135 (2014)). Since the majority of GvHD is observed when leukemia patients receive HSCT, echinomycin and other HIF inhibitors may be uniquely suited for treating GvHD and reducing relapse of leukemia.

The above description is for the purpose of teaching a person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method of treating GvHD in a mammalian subject receiving an allogeneic hematopoietic stem cell (HSC) transplant, comprising:
   administering to the subject an effective amount of a pharmaceutical composition comprising an active agent that inhibits the biological activity or expression of hypoxia-inducible factor-1a (HIF-1α) and/or hypoxia-inducible factor-2α (HIF-2α), wherein the active agent is echinomycin.

2. The method of claim 1, wherein the pharmaceutical composition is administered to the subject prior to transplantation of the HSCs or following transplantation of the HSCs.

3. The method of claim 1, wherein the pharmaceutical composition is administered to the subject prior to and following transplantation of the HSCs.

4. The method of claim 1, wherein the pharmaceutical composition is administered to the subject within the time period of 14 days before transplantation of the HSCs to 2 months after transplantation of the HSCs.

5. The method of claim 1, wherein the transplanted HSCs comprise the active agent.

6. The method of claim 1, wherein the transplant comprises embryonic stem cells or induced pluripotent stem cells from which the HSCs were derived.

7. The method of claim 1, wherein the subject has further received a transplant of mesenchymal stromal cells.

8. The method of claim 1, wherein the subject has leukemia or a non-hematopoietic disease.

9. The method of claim 1, wherein the composition further comprises a small molecule inhibitor of HIF-2α, or an additional small molecule inhibitor of HIF-1α.

10. The method of claim 1, wherein the composition further comprises a small molecule inhibitor selected from the group consisting of inhibitors of the interaction between HIF and DNA, inhibitors of the interaction between HIF-α and p300, inhibitors of HIF dimerization, topoisomerase I inhibitors, topoisomerase II inhibitors, heat shock protein-90 inhibitors, microtubule disrupting agents, hi stone deacetylase inhibitors, PI3-kinase inhibitors, and combinations thereof.

11. The method of claim 1, wherein the composition further comprises an siRNA directed against HIF-1α or HIF-2α.

12. The method of claim 1, wherein the composition further comprises one or more vectors encoding a gene editing system engineered to reduce, prevent or otherwise disrupt endogenous expression of HIF-1α or HIF-2α and wherein the one or more vectors are introduced into the HSCs.

13. The method of claim 12, wherein the gene editing system comprises a nuclease comprising a Clustered Regularly Interspaced Short Palindromic Repeats (CRISPR)-associated (Cas) protein, a zinc finger nuclease (ZFN), a Transcription Activator-Like Effector Nuclease (TALEN), or a meganuclease.

14. The method of claim 12, wherein the gene editing system comprises a Cas9 protein and a guide RNA (gRNA).

15. The method of claim 1, further comprising the step of monitoring expression of HIF-1α and/or HIF-2α in $CD4^+$ and/or $CD8^+$ T cells in the subject.

16. The method of claim 1, wherein the pharmaceutical composition is administered in combination with another agent for the treatment of GvHD.

17. The method of claim 16, wherein the other agent is an agent that enhances Treg activity.

18. A method of treating GvHD in a mammalian subject receiving an allogeneic hematopoietic stem cell (HSC) transplant, comprising:
administering to the subject an effective amount of a pharmaceutical composition comprising an active agent that inhibits the biological activity or expression of hypoxia-inducible factor-1a (HIF-1α) and/or hypoxia-inducible factor-2α (HIF-2α); and
monitoring expression of HIF-1α and/or HIF-2α in $CD4^+$ and/or $CD8^+$ T cells in the subject.

* * * * *